United States Patent
Mihovilovic et al.

(10) Patent No.: US 8,986,994 B2
(45) Date of Patent: Mar. 24, 2015

(54) SUBSTITUTED PYRIDINES AND PYRIMIDINES

(75) Inventors: Marko Mihovilovic, Perchtoldsdorf (AT); Michael Schnuerch, Steinbrunn Neue Siedlung (AT); Moumita Koley, Bangalore (IN); Karlheinz Hilber, Vienna (AT); Xaver Koenig, Moedling (AT)

(73) Assignee: Technische Universitaet Wien, Vienna (AT)

( * ) Notice: Subject to any disclaimer, the term of this patent is extended or adjusted under 35 U.S.C. 154(b) by 0 days.

(21) Appl. No.: 13/519,690

(22) PCT Filed: Dec. 28, 2010

(86) PCT No.: PCT/AT2010/000495
§ 371 (c)(1),
(2), (4) Date: Jul. 27, 2012

(87) PCT Pub. No.: WO2011/079343
PCT Pub. Date: Jul. 7, 2011

(65) Prior Publication Data
US 2012/0294835 A1    Nov. 22, 2012

(30) Foreign Application Priority Data
Dec. 28, 2009   (AT) ................ A 2044/2009

(51) Int. Cl.
*C12N 5/071*   (2010.01)
*C07D 239/48*  (2006.01)
*C07D 213/74*  (2006.01)
*C12N 5/077*   (2010.01)

(52) U.S. Cl.
CPC ............ *C07D 239/48* (2013.01); *C07D 213/74* (2013.01); *C12N 5/0657* (2013.01); *C12N 2500/40* (2013.01)
USPC ....................................... 435/377

(58) Field of Classification Search
None
See application file for complete search history.

(56) References Cited

FOREIGN PATENT DOCUMENTS

WO    WO 2005/068437 A1    7/2005

OTHER PUBLICATIONS

International Search Report issued Aug. 25, 2011 in Application No. PCT/AT2010/000495.
Yao Ma, et al., "Combinatorial Synthesis of Substituted Biaryls and Heterocyclic Arylamines", J. Comb. Chem., vol. 6, 2004, pp. 426-430.
Xu Wu, et al., "Small Molecules that Induce Cardiomyogenesis in Embryonic Stem Cells", J. Am. Chem. Soc., vol. 126, 2004, pp. 1590-1591.

*Primary Examiner* — Allison Fox
*Assistant Examiner* — Yvonne Pyla
(74) *Attorney, Agent, or Firm* — Leydig, Voit & Mayer, Ltd.

(57) ABSTRACT

Provided are compounds of formula (I) and/or salts thereof, of the class of substituted pyridines and pyrimidines, useful for inducing cardiomyogenesis, a process for producing cardiomyocyte-like cells from mammalian cells by culturing mammalian cells in the presence of the compound of formula (I), the pharmaceutical use of compounds of formula (I) for producing cardiomyocyte-like cells from omnipotent, pluripotent, or lineage committed mammalian cells, and the use of thus produced cardiomyocyte-like cells for treating disorders associated with impaired function of the heart.

19 Claims, No Drawings

SUBSTITUTED PYRIDINES AND PYRIMIDINES

CROSS REFERENCE TO RELATED APPLICATIONS

The present application is the national stage of international application PCT/AT2010/000495, filed on Dec. 28, 2010, and claims the benefit of the filing date of Austrian Application No. 2044/2009, filed on Dec. 28, 2009.

The present invention relates to substituted pyridines and pyrimidines which have been found to be pharmaceutically useful compounds. In particular, such compounds have a cardiomyogenic effect on omnipotent, pluripotent and lineage committed mammalian cells, which can be used for intra-cardiac transplantation to treat heart diseases.

The formation of cardiac myocytes (cardiomyocytes), or cardiomyocyte-like cells from transplanted mammalian cells in the heart of a patient is a very important task; e.g. it may result in a significant improvement of heart function after a myocardial infarction.

In the present invention, it was now surprisingly found that cardiomyocyte-like cells may be obtained not only from omnipotent or pluripotent mammalian cells, but also from lineage committed cells, such as skeletal muscle-committed cells—the skeletal myoblasts—when cultered in the presence of certain compounds which compounds are provided according to the present invention.

In one aspect the present invention provides a process for the production of cardiomocyte-like cells from cells, such as from omnipotent or pluripotent cells, and from cells other than omnipotent or pluripotent cells, e.g. from lineage committed cells, such as skeletal muscle-committed cells, e.g. the skeletal myoblasts, e.g. which cells are mammalian cells, comprising cultering cells in the presence of a compound of formula

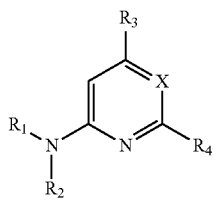

I wherein
X is CH or N,
$R_1$ and $R_2$ independently of each other are H, alkyl, aryl or cycloalkyl,
$R_3$ and $R_4$ independently of each other are H or $NR_5R_6$,
$R_5$ and $R_6$ independently of each other are H, alkyl, aryl or cycloalkyl;
or $R_1$ and $R_2$ together with the nitrogen atom to which they are attached form a heterocyclic ring, or
$R_1$ together with the nitrogen atom to which it is attached and together with a C-atom of the pyrimidine- or pyridine-ring forms a heterocyclic ring, or
$R_5$ and $R_6$ together with the nitrogen atom to which they are attached form a heterocyclic ring, or
if X is CH, $R_5$ together with the nitrogen atom to which it is attached and together with a C-atom of the X-comprising ring forms a heterocyclic ring,
with the proviso that $R_4$ is other than $NR_5R_6$, if X is N; e.g.
X is CH or N,
$R_1$ and $R_2$ independently of each other are H, alkyl, aryl or cycloalkyl,
$R_3$ is $NR_5R_6$,
$R_4$ is H, and
$R_5$ and $R_6$ independently of each other are H, alkyl, aryl or cycloalkyl;
or
X is CH,
$R_1$ and $R_2$ independently of each other are H, alkyl, aryl or cycloalkyl,
$R_3$ is H,
$R_4$ is $NR_5R_6$, and
$R_5$ and $R_6$ independently of each other are H, alkyl, aryl or cycloalkyl;
or
X is CH or N, preferably N,
$R_1$ and $R_2$ together with the nitrogen atom to which they are attached form heterocyclyl, e.g. aliphatic or aromatic, such as aliphatic heterocyclyl having 1 to 4 heteroatoms selected from N, and/or O and/or S, e.g. N and/or O, and having 3 to 8 ring members, e.g. 4 to 7, such as 6, and 1 to 4 heteroatoms, e.g. 2, selected from N and/or O and/or S, e.g. selected from N and O, such as morpholino,
$R_3$ is $NR_5R_6$,
$R_4$ is H, and
$R_5$ and $R_6$ independently of each other are H, alkyl, aryl or cycloalkyl;
or
X is CH or N, preferably N,
$R_1$ and $R_2$ independently of each other are H, alkyl, aryl or cycloalkyl;
$R_3$ is $NR_5R_6$,
$R_4$ is H, and
$R_5$ and $R_6$ together with the nitrogen atom to which they are attached form heterocyclyl, e.g. aliphatic or aromatic, such as aliphatic heterocyclyl having 1 to 4 heteroatoms selected from N, and/or O and/or S, e.g. N and/or O.

For the case that in a compound of formula I beside the pyrimidin or pyridine ring a second heterocyclic ring is formed it is preferred that said second heterocyclic ring is formed by
$R_1$ and $R_2$ together with the nitrogen atom to which they are attached, or by
$R_5$ and $R_6$ together with the nitrogen atom to which they are attached.

Cell culturing in a process provided by the present invention is carried out outside of the body.

In a compound of formula I preferably
$R_1$ is hydrogen, alkyl; such as $C_{1-4}$ alkyl, e.g. including $C_{1-2}$ alkyl substituted by aryl;
cycloalkyl, such as $C_{3-8}$ cycloalkyl; or aryl, such as $C_{6-12}$aryl; wherein alkyl, cycloalkyl or aryl are unsubstituted or substituted by 0-2 groups $R_{1a}$,
wherein $R_{1a}$ groups independently are selected from halogen, alkyl, e.g. $C_{1-4}$ alkyl, alkoxy, e.g. $C_{1-4}$alkoxy, —OH, —N($R_{1b}$,$R_{2b}$), —$SO_2$N($R_{1b}$,$R_{2b}$), —C(O)N($R_{1b}$,$R_{2b}$), heterocyclyl and —O-aryl, or
when $R_{1a}$ groups are bound to adjacent atoms, the $R_{1a}$ groups together optionally form a group —O—$(CH_2)_{1-2}$—O—, —OC$(CH_3)_2$$CH_2$— or —$(CH_2)_{3-4}$— group, or
$R_1$ and $R_2$ together with the nitrogen atom to which they are attached form a heterocyclic ring, which ring is optionally substituted by alkyl, such as $C_{1-4}$ alkyl, cycloalkyl, such as $C_{3-8}$cycloalkyl, hydroxyalkyl, such as hydroxy$C_{1-4}$alkyl, alkylaryl or aryl, such as $C_{0-2}$alkylaryl; or
$R_1$ together with the nitrogen atom to which it is attached and together with a C-atom of the pyrimidine- or pyridine-ring forms a ring, which ring is optionally substituted by alkyl, such as $C_{1-4}$ alkyl, cycloalkyl, such as $C_{3-8}$cycloalkyl, hydroxyalkyl, such as hydroxy$C_{1-4}$alkyl, alkylaryl or aryl, such as $C_{0-2}$alkylaryl; and each group $R_{1b}$ or $R_{2b}$ is independently selected from hydrogen and alkyl, such as $C_{1-4}$alkyl, or $R_{1b}$ or $R_{2b}$ together with the nitrogen atom to which they are attached form heterocyclyl.

In a compound of formula I preferably $R_2$ is hydrogen, alkyl, such as $C_{1-4}$ alkyl, e.g. including $C_{1-2}$ alkyl substituted by aryl; cycloalkyl such as $C_{3-8}$ cycloalkyl; or aryl, such as $C_{6-12}$aryl;

wherein alkyl, cycloalkyl or aryl optionally are substituted by 0-2 groups $R_{1a}$, wherein $R_{1a}$ is as defined above.

In a compound of formula I preferably $R_3$ is hydrogen, e.g. if X is CH; or is $NR_5R_6$, e.g. if X is CH or N.

In a compound of formula I preferably $R_4$ is hydrogen if X is N or CH; or is $NR_5R_6$ if X is CH.

In a compound of formula I preferably $R_5$ and $R_6$ have the meaning as set out herein for $R_1$ and $R_2$, respectively.

In one preferred aspect, in a compound of formula I $R_1$ is H or $(C_{1-4})$alkyl, such as methyl.

In a further preferred aspect, in a compound of formula I $R_2$ is
$(C_{1-8})$alkyl, e.g. $(C_{1-4})$alkyl,
$(C_{1-8})$hydroxyalkyl, e.g. $(C_{1-4})$hydroxalkyl,
$(C_{1-6})$alkoxy$(C_{1-6})$alkyl, e.g. $(C_{1-4})$alkoxy$(C_{1-4})$alkyl, such as methoxyethyl,
$(C_{1-6})$carboxyalkyl, e.g. $(C_{1-4})$carboxyalkyl, such as carboxymethyl,
$(C_{3-12})$cycloalkyl, e.g. $(C_{5-10})$cycloalkyl, such as cyclopentyl, cyclohexyl, adamantyl, e.g. adamantan-1-yl.
unsubstituted $(C_{6-12})$aryl, e.g. phenyl,
$(C_{6-12})$aryl, e.g. phenyl, substituted one or morefold, e.g. one or twofold, by
  $(C_{1-4})$alkoxy, such as methoxy,
  nitro,
  halogen, such as F, Cl, Br,
  $(C_{1-4})$alkoxycarbonyl, e.g. ethoxycarbonyl,
  unsubstituted amino,
  amino substituted by $(C_{6-12})$aryl, e.g. amino substituted by phenyl,
  $(C_{6-12})$aryloxy, e.g. phenoxy),
heterocyclyl, e.g. aliphatic or aromatic, preferably aliphatic, having 3 to 8 ring members, e.g. 4 to 7, such as 5, and 1 to 4 heteroatoms, e.g. 2, selected from N and/or O and/or S, e.g. selected from N and O, such as morpholino.

In another preferred aspect, in a compound of formula I $R_1$ and $R_2$ together with the nitrogen atom to which they are attached form heterocyclyl.

In another aspect the present invention provides a compound of formula I, wherein
—X is N or CH, e.g. and/or
$R_1$ is
  $(C_{1-8})$alkyl, such as $(C_{1-6})$alkyl, e.g. methyl, ethyl, n-propyl, isopropyl, n-butyl, isobutyl, tert-butyl;
  $(C_{1-4})$hydroxyalkyl, e.g. 2-hydroxyethyl, 3-hydroxypropyl;
  $(C_{1-4})$alkoxy-$(C_{1-4})$alkyl, such as 2-methoxy-ethyl; carboxy$(C_{1-6})$alkyl, e.g. carboxymethyl;
  $(C_{3-12})$cycloalkyl, e.g. cyclopentyl, cyclohexyl, admantan-1-yl,
  unsubstituted $(C_{6-12})$aryl, e.g. phenyl,
  $(C_{6-12})$aryl, e.g. phenyl, substituted one or morefold, e.g. one or twofold, by
    $(C_{1-4})$alkoxy, such as methoxy, e.g. 3-methoxyphenyl, 4-methoxyphenyl,
    nitro, e.g. 3-nitro-phenyl, 4-nitro-phenyl,
    halogen, such as F, Cl, Br, e.g. 3-fluoro-phenyl, 3-chlorophenyl, 3-bromo-phenyl, 4-chloro-phenyl, 3-chloro-4-methoxycarbonyl-phenyl,
    $(C_{1-4})$alkoxycarbonyl, such as ethoxycarbonyl, e.g. 4-ethoxycarbonyl-phenyl,
    unsubstituted or substituted, preferably substituted amino, such as amino substituted by
      $(C_{6-12})$aryl, e.g. amino substituted by phenyl, e.g. 4-(phenylamino)-phenyl;
    $(C_{6-12})$aryloxy, such as phenoxy, e.g. 4-(phenoxy)-phenyl,
    heterocyclyl, e.g. aliphatic or aromatic, preferably aliphatic, having 3 to 8 ring members, e.g. 4 to 7, such as 5, and 1 to 4 heteroatoms, e.g. 2, selected from N and/or O and/or S, e.g. selected from N and O, such as morpholino, e.g. morpholin-1-yl-phenyl; e.g. and/or
$R_2$ is H or $(C_{1-4})$alkyl, such as methyl; e.g. and or
$R_3$ is H or $NR_5R_6$, e.g. $R_3$ is H, if X is CH; or, $R_3$ is $NR_5R_6$, if X is N or CH; e.g. and/or
$R_4$ is H or $NR_5R_6$, e.g. $R_4$ is H, if X is N or CH; or, $R_4$ is $NR_5R_6$, if X is CH; e.g. and/or
$R_5$ is as defined for $R_1$; e.g. and/or
$R_6$ is as defined for $R_2$; or
$R_1$ and $R_2$, or $R_5$ and $R_6$ together with the nitrogen atom to which they are attached form heterocylclyl, e.g. aliphatic or aromatic, preferably aliphatic, having 3 to 8 ring members, e.g. 4 to 7, such as 5, and 1 to 4 heteroatoms, e.g. 2, selected from N and/or O and/or S, e.g. selected from N and O, such as morpholino.

In a further aspect the present invention provides a compound of formula I,
wherein
$R_1$ is $C_{3-8}$cycloalkyl or $C_{1-3}$alkyl, optionally substituted by hydroxy,
  e.g. $C_{1-3}$alkyl is unsubstituted or substituted by hydroxy and $C_{3-8}$cycloalkyl is unsubstituted,
  e.g. $R_1$ is methyl, ethyl, propyl, such as n-propyl, isopropyl, hydroxyethyl, such as 2-hydroxyethyl, hydroxypropyl, such as 3-hydroxypropyl, cyclohexyl; and/or
$R_2$ is H; and/or
$R_3$ is H, if X is CH; or, $R_3$ is $NR_5R_6$, if X is N or CH; and/or
$R_4$ is H, if X is N or CH; or, $R_4$ is $NR_5R_6$, if X is CH; and/or
$R_5$ is methoxyphenyl, such as 3-methoxyphenyl, 4-methoxyphenyl; morpholinylphenyl, such as 4-morpholin-1-yl-phenyl, phenylaminophenyl, such as 4-phenylaminophenyl, phenoxyphenyl, such as 4-phenoxy-phenyl; and/or
$R_6$ is H.

In a compound of formula I each single group of substitutents defined may be a preferred group of substitutents, e.g. independently of each other group of substitutents or single substitutent defined. In a compound of formula I each single substitutent defined, may be a preferred substituent, e.g. independently of each other group of substitutents or single substitutent defined.

In another aspect the present invention provides a compound selected from, e.g. the group consisting of,
2-(6-(4-Methoxyphenylamino)pyrimidine-4-ylamino)ethan-1-ol,
3-(6-(4-Methoxyphenylamino)pyrimidine-4-ylamino)propan-1-ol,
$N^4$-Cyclohexyl-$N^6$-(4-methoxyphenyl)pyrimidine-4,6-diamine, 2-(6-(4-Morpholinophenylamino)pyrimidin-4-ylamino)
    ethan-1-ol,
$N^4$-Cyclohexyl-$N^6$-(4-morpholinophenyl)pyrimidine-4,6-
    diamine,
3-(6-(4-Morpholinophenylamino)pyrimidin-4-ylamino)pro-
    pan-1-ol,
2-(6-(4-(Phenylamino)phenylamino)pyrimidin-4-ylamino)
    ethan-1-ol,
2-(6-(4-Phenoxyphenylamino)pyrimidin-4-ylamino)ethan-
    1-ol,
$N^4$-(4-Methoxyphenyl)-$N^6$-propylpyrimidine-4,6-diamine,
$N^4$-Ethyl-$N^6$-(4-methoxyphenyl)pyrimidine-4,6-diamine,
$N^4$-(4-Methoxyphenyl)-$N^6$-methylpyrimidine-4,6-diamine,
$N^4$-(2-Propyl)-$N^6$-(4-methoxyphenyl)pyrimidine-4,6-di-
    amine,
$N^4$-(2-Methoxyethyl)-$N^6$-(4-methoxyphenyl)pyrimidine-4,
    6-diamine,
2-(6-(4-Methoxyphenylamino)pyrimidin-4-ylamino)acetic
    acid,
N-(4-Methoxyphenyl)-6-morpholinopyrimidin-4-amine,
2-((6-(4-Methoxyphenylamino)pyrimidin-4-yl)(methyl)
    amino)ethan-1-ol,
$N^4$-Butyl-$N^6$-(4-methoxyphenyl)pyrimidine-4,6-diamine,
$N^4$-Cyclopentyl-$N^6$-(4-methoxyphenyl)pyrimidine-4,6-di-
    amine,
$N^4$-sec-Butyl-N-6-(4-methoxyphenyl)pyrimidine-4,6-di-
    amine,
$N^4$-tert-Butyl-$N^6$-(4-methoxyphenyl)pyrimidine-4,6-di-
    amine,
$N^4$-Adamant-1-yl-$N^6$-(4-methoxyphenyl)pyrimidine-4,6-di-
    amine,
2-(6-(3-Methoxyphenylamino)pyrimidin-4-ylamino)ethan-
    1-ol,
2-(6-(Phenylamino)pyrimidin-4-ylamino)ethan-1-ol,
2-(6-(4-Chlorophenylamino)pyrimidin-4-ylamino)ethan-1-
    ol,
2-(6-(3-Chlorophenylamino)pyrimidin-4-ylamino)ethan-1-
    ol,
$N^4$-(3-Chlorophenyl)-$N^6$-cyclohexylpyrimidine-4,6-di-
    amine,
$N^4$-(3-Chlorophenyl)-$N^6$-(2-methoxyethyl)pyrimidine-4,6-
    diamine,
2-(6-(3-Nitrophenylamino)pyrimidin-4-ylamino)ethanol,
$N^4$-Cyclohexyl-$N^6$-(3-nitrophenyl)pyrimidine-4,6-diamine,
2-(6-(4-Nitrophenylamino)pyrimidin-4-ylamino)ethan-1-ol,
3-(6-(3-Chlorophenylamino)pyrimidin-4-ylamino)propan-
    1-ol,
2-(6-(3-Fluorophenylamino)pyrimidin-4-ylamino)ethan-1-
    ol,
2-(6-(3-Bromophenylamino)pyrimidin-4-ylamino)ethan-1-
    ol,
Ethyl 4-(6-(2-hydroxyethylamino)pyrimidin-4-ylamino)
    benzoate,
2-(6-(3-Chloro-4-methoxyphenylamino)pyrimidin-4-
    ylamino)ethanol,
$N^4$-(3-Chloro-4-methoxyphenyl)-$N^6$-cyclohexylpyrimidine-
    4,6-diamine,
$N^4$-Cyclohexyl-$N^6$-(3-methoxyphenyl)pyrimidine-4,6-di-
    amine,
2-(6-((4-Methoxyphenyl)(methyl)amino)pyrimidin-4-
    ylamino)ethan-1-ol,
2-(6-(Cyclohexylamino)pyrimidin-4-ylamino)ethan-1-ol,
2-(4-(4-Methoxyphenylamino)pyridin-2-ylamino)ethan-1-
    ol,
2-(4-(4-Phenoxyphenylamino)pyridin-2-ylamino)ethan-1-
    ol,
2-(6-(4-Methoxyphenylamino)pyridin-2-ylamino)ethan-1-
    ol,
3-(6-(4-Methoxyphenylamino)pyridin-2-ylamino)propan-1-
    ol,
2-(6-(4-Phenoxyphenylamino)pyridin-2-ylamino)ethan-1-
    ol, and
3-(6-(4-Phenoxyphenylamino)pyridin-2-ylamino)propan-1-
    ol.
e.g. a compounds as set out in Examples 1 to 45.

If not specifically otherwise defined herein, any group (substituent) defined herein may comprise 1 to 18 carbon atoms, for example
    alkyl e.g. includes $(C_{1-4})$alkyl,
    cycloalkyl e.g. includes $(C_{3-8})$cycloalkyl,
    alkoxy e.g. includes $(C_{1-4})$alkoxy,
    aryl includes $(C_{6-18})$aryl, e.g. phenyl,
    arylalkyl e.g. includes $(C_{6-18})$aryl$(C_{1-2})$alkyl,
    heterocyclyl and heterocyclic ring e.g. includes
        aliphatic heterocyclyl and aromatic heterocyclyl,
        4 to 8 membered heterocyclyl,
        heterocyclyl optionally anellated with another ring (system), e.g. anellated with aryl; e.g. or anellated with a heterocyclic ring (system);
        heterocyclyl having 1 to 4 heteroatoms selected from N, O, S;
    e.g. including morpholinyl;
    halogen includes F, Cl, Br, I.
Any group defined herein may be unsubstituted or substituted, e.g. one or morefold, e.g. by substitutents as conventional in organic chemistry, e.g. as set out above.

Compounds provided by the present invention are hereinafter designated as "compound(s) of (according to) the present invention".

A compound of the present invention includes a compound in any form, e.g. in free form and in the form of cocrystals, such as in the form of a salt, in the form of a solvate and in the form of a salt and a solvate.

In another aspect the present invention provides a compound of the present invention in the form of a salt.

Such salts include preferably pharmaceutically acceptable salts, although pharmaceutically unacceptable salts are included, e.g. for preparation/isolation/purification purposes.

A salt of a compound of the present invention includes a metal salt or an acid addition salt. Metal salts include for example alkali or earth alkali salts; acid addition salts include salts of a compound of formula I with an acid, A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention optionally may exist in the form of isomers and mixtures thereof; e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates. A compound of the present invention may be present in the (R)-, (S)- or (R,S)-configuration preferably in the (R)- or (S)-configuration regarding each of the substituents at such asymmetric carbon atoms in a compound of the present invention, e.g. in case that a cyloalkyl group is present.

Isomeric mixtures may be separated as appropriate, e.g. according, e.g. analogously, to a method as conventional, to obtain pure isomers. The present invention includes a compound of the present invention in any isomeric form and in any isomeric mixture.

The present invention also includes tautomers of a compound of the present invention, where tautomers can exist.

In another aspect the present invention provides a process for the production of a compound of the present invention, e.g. of formula I, comprising the steps of reacting a compound of formula

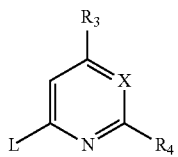

II wherein X, $R_3$ and $R_4$ are as defined above and L is a leaving group, e.g. halogen, with a compound of formula $NHR_1R_2$ wherein $R_1$ and $R_2$ are as defined above and isolating a compound of formula I, wherein X, $R_1$, $R_2$, $R_3$ and $R_4$ obtained from the reaction mixture.

In an intermediate of formula II or (starting materials), functional groups, if present, optionally may be in protected form or in the form of a salt, if a salt-forming group is present. Protecting groups, optionally present, may be removed at an appropriate stage, e.g. according, e.g. analogously, to a method as conventional.

A compound of formula I thus obtained may be converted into another compound of formula I, e.g. or a compound of formula I obtained in free form may be converted into a salt of a compound of formula I and vice versa.

The above reaction is a substitution reaction and may be carried out as appropriate, e.g. analogously to a method as conventional, or e.g. as set out herein.

Intermediates (starting materials) of formula II are known or may be prepared according, e.g. analogously, to a method as conventional or as specified herein.

Any compound described herein, e.g. a compound of the present invention and intermediates of formula II may be prepared as appropriate, e.g. according, e.g. analogously, to a method as conventional, e.g. or as specified herein.

It was found that cardiomyocyte-like cells may be obtained from skeletal myoblasts when cultered in the presence of a compound of the present invention and thus compounds of the present invention, e.g. including a compound of formula I, have been found to generate a cardiomyogenic effect, and thus may be useful as pharmaceuticals.

That activity of the compounds of the present invention may be shown by the following BIOLOGICAL TEST METHOD:
Biological Test Method
(Methodological Approaches for Biological Testing)
Cell Types
C2C12 skeletal myoblasts (American Type Culture Collection, ATCC), P19 embryonal carcinoma cells (ATCC)
Cell Culture
C2C12 cells are propagated in growth medium consisting of Dulbecco's modified Eagle's medium (DMEM) containing 4.5 g/l glucose, 4 mM L-glutamine, 50 U/ml penicillin, 50 g/ml streptomycin, and 20% fetal calf serum. The cells are incubated at 37° C. and 5% $CO_2$, and when about 50-70% confluence is reached, in undifferentiated skeletal muscle cells (myoblasts), differentiation is induced by serum reduction. For this purpose, myoblasts are incubated in differentiation medium that is identical to the growth medium, except that it contains 2% horse serum instead of 20% fetal calf serum. Small molecules to be tested are always added at the same time as differentiation is induced. DMSO, which is used as solvent for the small molecules, is added in equal amounts to "control cells". The media are changed three times per week.

P19 cells are cultured in monolayers in MEM-alpha medium with 7.5% new born calf serum and 2.5% FBS at 37° C. in 5% $CO_2$. At about 60% cell confluence, the small molecules to be tested are added. DMSO, which is used as solvent for the small molecules, is added in equal amounts to "control cells". The media are changed three times per week.

Assessment of Cardiomyogenic Activity of the Small Molecules

1) In order to be able to screen a large number of small molecules for their cardiomyogenic activity in a short time (high throughput screen), we use an ANF promoter reporter assay. In this assay, an up-regulation of the expression of ANF is reported by an increased luciferase activity. ANF (atrial natriuretic factor) is a polypeptide hormone synthesized primarily in cardiomyocytes, and considered a specific cardiomyocyte marker gene. For the assay, a fragment containing the rat ANF promoter region was amplified and then subcloned into the PGL3-BV luciferase reporter plasmid. C2C12 and P19 cells transiently transfected with this plasmid are selected for the screening experiments. In these experiments, cells plated on 48 or 96 well plates are either cultivated in normal medium (control cells) or in media containing various single small molecules (experimental groups) in a concentration of 1 µM for 8 days. Thereafter, the luciferase activity is measured. A significant up-regulation of ANF (indicated by an increased luciferase signal) by a small molecule found using this assay is the first indicator of its cardiomyogenic activity.

2) Only if a small molecule significantly up-regulates ANF in the described reporter assay, the expression of ANF and other classical cardiac markers are tested, at different time points (1-12 days of treatment), in RT-PCR experiments. The following markers are used: ANF, GATA4, NRx2.5, α-myosin heavy chain, myosin light chains 2a and 2v.

3) Electrophysiological experiments: To test if small molecules also induce cardiomyogenic function besides the induction of cardiac markers, their effects on the electrophysiological properties of the cells are tested. Therefore, only small molecules with proven cardiomyogenic activity in the above described experiments (1 and 2) are further investigated in whole cell patch clamp studies. Ionic currents in untreated and small molecule-treated cells are compared at various time points (1-12 days of treatment). Na currents are recorded at room temperature (22±1.5° C.) with an Axoclamp 200B patch-clamp amplifier. Pipettes are formed from aluminosilicate glass (AF150-100-10; Science Products) with a P-97 horizontal puller (Sutter Instruments) and have resistances between 1 and 2 mega ohms when filled with the recording pipette solution (105 mM CsF, 10 mM NaCl, 10 mM EGTA, and 10 mM HEPES, pH 7.3). Voltage-clamp protocols and data acquisition are performed with pCLAMP 6.0 software (Axon Instruments) via a 12-bit A/D-D/A interface (Digidata 1200; Axon Instruments). A bathing solution consisting of 140 mM NaCl, 2.5 mM KCl, 1 mM $CaCl_2$, 1 mM $MgCl_2$, and 10 mM HEPES, pH 7.4, is used to obtain recordings. If Na currents are induced by small molecule-treatment, their cardiac nature is verified. Therefore, the expression of the cardiac Na channel isoform Nav1.5 in skeletal myocytes is proven by a) the detection of its characteristic properties (e.g. slow kinetics of entry into fast inactivation and slow inactivation resistance compared to adult skeletal muscle Nav1.4 channels or Nav1.1 and Nav1.2 brain channels), b) tetrodotoxin (TTX) experiments (Nav1.5 is TTX-resistant!), and c) RT-PCR analyses. Ca currents are elicited from a holding potential of −80 mV by depolarising voltage steps between −50 and +80 mV in 10 mV increments. A 1-s prepulse to −50 mV preceding the test pulses can be applied to inactivate T-type Ca channels. This generates clean L-type Ca currents, which will be checked by using nitrendipine (10 µM), a selective L-type Ca channel blocker. Steady state inactivation is tested by steps to −10 mV from various holding potentials (HPs). Besides Ca, also Ba is used as charge carrier to distinguish between Ca- and voltage-dependent inactivation. The external solution contains (in mM): 10 $CaCl_2$, 145 Tetraethylammonium chloride (TEA-Cl), 10 HEPES (pH 7.4 with TEA-OH). 10 $CaCl_2$ is substituted by 10 $BaCl_2$ when Ba is desired as charge carrier. The internal solution contains 145 cesium aspartate, 2 $MgCl_2$, 10 HEPES, 0.1 Cs-EGTA, 2 Mg-ATP (pH 7.4 with CsOH). For Ca currents, the main cardiac L-type Ca channel isoform Cav1.2 can be identified by its rapid activation kinetics compared to skeletal muscle Cav1.1 channels. Besides voltage-dependent inactivation, Cav1.2 (but not Cav1.1) shows additional Ca-dependent inactivation. Finally, PCR experiments can ultimately clarify which Ca channel isoforms contribute to the measured Ca currents. Action potential recordings: Action potentials are recorded in the current-clamp configuration using standard solutions and procedures. Briefly, after establishment of the whole cell condition in the voltage-clamp mode and compensation for the pipette capacitance, cells are current clamped to a resting membrane potential of −80 mV. Action potentials are then elicited by 2-ms depolarising pulses at 1 Hz. Cardiac versus skeletal muscle or neuronal action potentials can easily be discriminated by their prolonged duration.

Experimental Results
Luciferase Reporter Assays

Compounds of the present invention show activity in these assays, e.g. the compounds obtained according to examples 3, 10, 12, 42 and 43 (1 µM for 8 days) generate an increase in the luciferase signal in all three reporter assays (see Table 1). This indicates an up-regulation of the expression of the respective cardiac marker genes in C2C12 cells, which are treated with these compounds and suggests strong cardiomyogenic effects. To our knowledge, this is the first report of small molecule-induced cardiomyogenic effects on lineage (skeletal muscle)-committed cells. Besides these highly active compounds, other compounds show activities not in all three assays, but in one or two out of the three assays (see Table 1).

TABLE 1

| | C2C12 cells | | | | | |
|---|---|---|---|---|---|---|
| | ANF | | TOPflash | | Nkx2.5 | |
| substance | activity | n | activity | n | activity | n |
| example 1 | ++ | 5 | − | 2 | − | 2 |
| example 2 | − | 4 | − | 2 | + | 2 |
| example 3 | ++ | 5 | + | 2 | ++ | 2 |
| example 4 | − | 4 | − | 2 | − | 2 |
| example 5 | − | 3 | − | 2 | − | 2 |
| example 6 | + | 3 | − | 2 | + | 2 |
| example 7 | − | 3 | − | 2 | − | 2 |
| example 8 | − | 3 | − | 2 | + | 2 |
| example 9 | − | 2 | + | 2 | + | 2 |
| example 10 | + | 2 | + | 2 | + | 2 |
| example 11 | − | 3 | + | 2 | + | 2 |
| example 12 | + | 3 | + | 2 | + | 2 |
| example 22 | + | 3 | + | 1 | − | 2 |
| example 40 | − | 3 | − | 2 | − | 2 |
| example 42 | + | 5 | + | 4 | + | 4 |
| example 43 | + | 2 | + | 2 | + | 2 |
| example 44 | − | 2 | − | 2 | + | 2 |
| example 45 | − | 2 | + | 2 | − | 1 |

Legend: The table summarises the "cardiomyogenic activities" estimated from the ANF, TOPflash, and NRx2.5 luciferase reporter assays of the small molecule compounds in C2C12 cells. + indicates cardiomyogenic activity and represents an increase in the luciferase signal between 1.3 and 2.0-fold compared to the control (untreated cells). ++ indicates strong activity (>2-fold increase in the luciferase signal). − indicates no activity (<1.3-fold increase in the luciferase signal). n gives the number of experiments performed.

Electrophysiological Testing

The compounds obtained according to examples 1 and 2 (1 µM for 8 days) moderately increase the tetrodotoxin (TTX)-resistance of the Na currents in C2C12 cells. This indicates an up-regulation of the expression of the cardiac Na channel isoform Nav1.5. Moreover, the compound obtained according to example 1 significantly speeds the activation kinetics of Ca currents in C2C12 cells. This effect is particularly interesting, because compared to skeletal muscle Ca channels, cardiac Ca channels activate much faster. Thus, treatment with a compound obtained according to example 1 generates more cardiac-like Na and Ca currents in C2C12 cells. Importantly, these data support that a compound obtained according to example 1 induces cardiomyogenic function by up-regulation of cardiac ion channels in C2C12 skeletal myoblasts.

b. P19 Cells
Luciferase Reporter Assays

Retinoic acid (1 µM for 8 days), a known inducer of cardiogenesis, potently increases the luciferase signal in all three reporter assays, indicating an up-regulation of the expression of cardiac marker genes in retinoic acid-treated P19 cells: This serves as a positive control. The compounds obtained according to examples 3 and 42 (1 µM for 8 days) generate an increase in the luciferase signal in all three reporter assays (see Table 2). This indicates an up-regulation of the expression of the respective cardiac marker genes in P19 cells, which are treated with these compounds and suggests strong cardiomyogenic effects. Besides these highly active compounds, other compounds show activities not in all three assays, but in one or two out of the three assays (see Table 2).

TABLE 2

| | P19 cells | | | | | |
|---|---|---|---|---|---|---|
| | ANF | | TOPflash | | Nkx2.5 | |
| substance | activity | n | activity | n | activity | N |
| example 1 | + | 3 | − | 1 | − | 3 |
| example 2 | + | 5 | ++ | 1 | − | 3 |

TABLE 2-continued

| | P19 cells | | | | | |
|---|---|---|---|---|---|---|
| | ANF | | TOPflash | | Nkx2.5 | |
| substance | activity | n | activity | n | activity | N |
| example 3 | ++ | 5 | ++ | 2 | ++ | 4 |
| example 4 | − | 3 | + | 2 | − | 3 |
| example 5 | + | 5 | − | 2 | − | 3 |
| example 6 | + | 3 | − | 2 | − | 3 |
| example 7 | − | 4 | − | 2 | − | 3 |
| example 8 | − | 4 | + | 2 | − | 3 |
| example 9 | − | 1 | − | 2 | ++ | 3 |
| example 10 | + | 3 | − | 2 | − | 3 |
| example 11 | − | 3 | ++ | 2 | − | 3 |
| example 12 | − | 3 | − | 2 | + | 2 |
| example 13 | + | 1 | | | | |
| example 14 | ++ | 1 | | | | |
| example 15 | ++ | 1 | | | | |
| example 16 | ++ | 1 | | | | |
| example 17 | ++ | 1 | | | | |
| example 18 | ++ | 1 | | | | |
| example 19 | − | 2 | | | − | 1 |
| example 20 | ++ | 1 | | | | |
| example 21 | ++ | 1 | | | | |
| example 22 | − | 3 | − | 2 | − | 3 |
| example 23 | − | 2 | | | − | 1 |
| example 24 | + | 2 | | | + | 1 |
| example 25 | ++ | 2 | | | + | 1 |
| example 26 | ++ | 1 | | | ++ | 1 |
| example 27 | − | 1 | | | − | 1 |
| example 30 | − | 1 | | | − | 1 |
| example 31 | + | 1 | | | + | 1 |
| example 32 | − | 1 | | | − | 1 |
| example 33 | − | 1 | | | + | 1 |
| example 34 | − | 1 | | | − | 1 |
| example 37 | + | 1 | | | ++ | 1 |
| example 38 | ++ | 1 | | | | |
| example 39 | − | 1 | | | | |
| example 40 | − | 3 | − | 2 | − | 3 |
| example 42 | + | 5 | ++ | 4 | + | 6 |
| example 43 | + | 2 | + | 2 | − | 3 |
| example 44 | + | 2 | − | 2 | − | 3 |
| example 45 | − | 3 | − | 2 | − | 3 |

Legend: The table summarises the "cardiomyogenic activities" estimated from the ANF, TOPflash, and NRx2.5 luciferase reporter assays of the small molecule compounds in P19 cells. + indicates cardiomyogenic activity and represents an increase in the luciferase signal between 1.3 and 2.0-fold compared to the control (untreated cells). ++ indicates strong activity (>2-fold increase in the luciferase signal). − indicates no activity (<1.3-fold increase in the luciferase signal). n gives the number of experiments performed.

Taken together, compounds of the present invention generate cardiomyogenic effects in C2C12 skeletal myoblasts and/or P19 embryonal carcinoma cells. The compounds obtained according to examples 3 and 42 are preferred compounds; e.g. they are effective in all three luciferase reporter assays and on both cell types tested. Thus, remarkably, their cardiomyogenic effect is not restricted to pluripotent stem cells (P19), but also applies to skeletal muscle-committed stem cells (C2C12 myoblasts). Moreover, besides the up-regulation of the cardiac marker ANF in both cell types, the compound obtained according to example 1 also generates more cardiac-like ionic currents in C2C12 cells, and thus, induces cardiomyogenic function.

c. Human Primary Skeletal Myoblasts
ANF-Reporter Assay

In two experiments, the compound obtained according to example 42 (1 µM for 6 days) generated an increase in the luciferase signal in the ANF reporter assay. Importantly, these data suggest that this specific, and probably also other small molecule compounds, exert cardiomyogenic effects also on human skeletal myoblasts. Thus, the compound obtained according to example 42, besides strong activity on mouse P19 and C2C12 cells (see above), also shows a similar activity in a human cell system.

Compounds of the present invention show activity in the BIOLOGICAL TEST METHOD described above and are therefore potential candidates to be used for the treatment of cardiac disorders (diseases), which go along with impaired cardiac function.

In particular, compounds of the present invention may be used to produce cardiomyocyte-like cells from omnipotent, pluripotent or lineage committed mammalian cells. This may not only be achieved in model stem cells (e.g. P19 cells or C2C12 cells), but also in cells derived from a heart patient prior to cell transplantation e.g. skeletal myoblasts.

Such treatment may e.g. be carried out by intra-cardiac injection of cardiomyocyte-like cells which are produced by treating omnipotent, pluripotent or lineage committed mammalian cells with a compound of the present invention. Such treatment may result in the regeneration of damaged heart regions e.g. after myocardial infarction and may improve heart function.

In particular, compounds of the present invention may be used to produce cardiomyocyte-like cells from cells originating from a patient, whose cardiomyocyte-like cells in consequence may be used for the treatment of disorders associated with the heart. Such treatment may e.g. be carried out by injection of cardiomyocyte-like cells which are produced by treating omnipotent, pluripotent or lineage committed mammalian cells with a compound of the present invention. Such treatment may improve damaged regions of the heart and may induce improved regeneration in regions which are damaged e.g. damaged by heart infarction.

In another aspect the present invention provides
 a compound of the present invention for pharmaceutical use,
 the pharmaceutical use of a compound of the present invention,
e.g. for the treatment of omnipotent, pluripotent or lineage committed mammalian cells to produce cardiomyocyte-like cells.

Such treatment may e.g. be carried out by intra-cardiac injection of cardiomyocyte-like cells which are produced by treating omnipotent, pluripotent or lineage committed mammalian cells with a compound of the present invention. Such treatment may result in the regeneration of damaged heart regions e.g. after myocardial infarction and may improve heart function.

In particular, compounds of the present invention may be used to produce cardiomyocyte-like cells from cells originating from a patient, whose cardiomyocyte-like cells in consequence may be used for the treatment of disorders associated with the heart. Such treatment may e.g. be carried out by injection of cardiomyocyte-like cells which are produced by treating omnipotent, pluripotent or lineage committed mammalian cells with a compound of the present invention. Such treatment may improve damaged regions of the heart and may induce improved regeneration in regions which are damaged e.g. damaged by heart infarction.

In another aspect the present invention provides
 a compound of the present invention for pharmaceutical use,
 the pharmaceutical use of a compound of the present invention, e.g. for the treatment of omnipotent, pluripotent or lineage committed mammalian cells to produce cardiomyocyte-like cells.

In particular, compounds of the present invention may be used to produce cardiomyocyte-like cells from omnipotent, pluripotent or lineage committed cells, e.g. including mammalian cells, such as P19 cells or C2C12 cells, of a patient, e.g. such which are originating form the own body, which cardiomyocyte-like cells in consequence may be used for the treatment of disorders associated with the heart. Such treatment may e.g. be carried out by injection of cardiomyocyte-like cells which are produced by treating omnipotent, pluripotent or lineage committed mammalian cells with a compound of the present invention. Such treatment may improve damaged regions of the heart and may induce improved regeneration in regions which are damaged e.g. damaged by heart infarction.

In another aspect the present invention provides
a compound of the present invention for pharmaceutical use,
the pharmaceutical use of a compound of the present invention,
e.g. for the treatment of omnipotent, pluripotent or lineage committed mammalian cells to produce cardiomyocyte-like cells.

Cardiomyocyte-like cells thus produced may be administered in a therapeutically effective amount, e.g. parenterally, to a subject in need of such treatment.

In a further aspect the present invention provides a method of treating cardiac disorders, E:G: disorders which are associated with an impaired function of the heart, comprising the steps of
(i) providing omnipotent, pluripotent or lineage committed cells, e.g. skeletal myoblasts, from a subject in need of such treatment,
(ii) culturing said cells in the presence of a compound of the present invention to produce cardiomyocyte-like cells, and
(iii) administering to the subject in need of such treatment a therapeutically effective amount of cardiomyocyte-like cells as produced in step (ii).

Treatment with cardiomyocyte-like cells produced according to a method provided by the present invention may be combined with other strategies to treat cardiac diseases.

In a further aspect the present invention provides
A compound as defined above for use in the production of cardiomyocyte-like cells, which production comprises treating omnipotent, pluripotent or lineage committed mammalian cells with a compound provided by the present invention;
A compound as defined in above for use in the treatment of disorders which are associated with an impaired function of the heart;
A compound as defined above for use in the preparation of an agent, e.g. which agent consists of cardiomyocyte-like cells, for the treatment of disorders which are associated with an impaired function of the heart.

In the following Examples all temperatures are indicated in degree Celsius (° C.) and are uncorrected.

The following abbreviations are used:

| BINAP | 2,2'-bis(diphenylphosphino)-1,1'-binaphthyl |
| DIPEA | diisopropylethylamine |
| EtOH | ethanol |
| EtOAc | ethyl acetate |
| HR-MS | high resolution mass spectroscopy |
| i-PrOH | 2-propanol |

-continued

| M.p. | melting point |
| MPLC | medium pressure liquid chromatoraphy |
| n-BuOH | n-butanol |
| PE | petroleum ether |
| r.t. | room temperature |
| TLC | thin layer chromatography |

EXAMPLE 1

2-(6-(4-Methoxyphenylamino)pyrimidine-4-ylamino)ethan-1-ol 1.a 6-Chloro-N-(4-methoxyphenyl)pyrimidine-4-amine

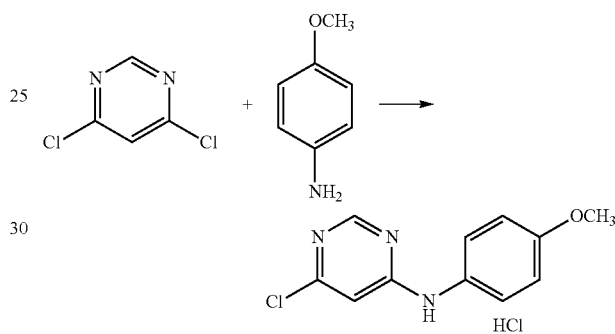

1.57 g of 4,6-dichloropyrimidine and 1 g of p-methoxyaniline were dissolved in 15 mL of i-PrOH and to the mixture obtained 1.5 mL of 37% HCl were added. The mixture obtained was refluxed for 2.5 hours under a nitrogen atmosphere. A colorless precipitate was formed which was collected by filtration. 6-Chloro-N-(4-methoxyphenyl)pyrimidine-4-amine in the form of a hydrochloride was obtained in the form of colorless crystals.

Yield: 56% of theory.

M.p.: 121-123° C.

$^1$H NMR (DMSO-D$_6$, 200 MHz): δ=3.75 (s, 3H), 3.72 (s, 1H), 6.95 (d, J=8.6 Hz, 2H), 7.49 (d, J=8.8 Hz, 2H), 8.38 (s, 1H), 9.89 (s, 1H).

$^{13}$C NMR (DMSO-D$_6$, 50 MHz): δ=55.3 (q), 104.1 (d), 114.1 (d), 122.6 (s), 131.6 (s), 155.7 (s), 157.1 (s), 158.1 (d), 161.3 (s).

1b. 2-(6-(4-Methoxyphenylamino)pyrimidine-4-ylamino)ethan-1-ol

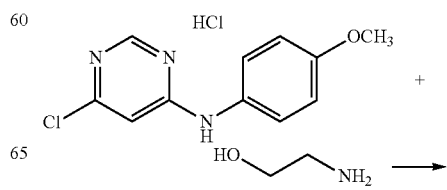

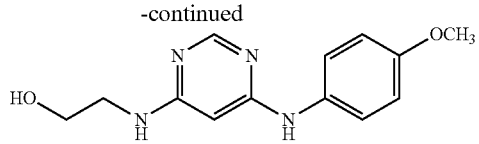

250 mg of 6-chloro-N-(4-methoxyphenyl)pyrimidine-4-amine in the form of a hydrochloride, 62 mg of ethanolamine and 296 mg of DIPEA were dissolved in 2 mL of n-BuOH and the mixture obtained was charged into a microwave vial and the vial obtained was heated to 200° C. for 45 minutes under microwave irradiation. Progress of the reaction was monitored by TLC. Upon termination of the reaction n-BuOH was evaporated. The evaporation residue was subjected to crystallization from an n-BuOH/EtOH solvent mixture.

3-(6-(4-Methoxyphenylamino)pyrimidine-4-ylamino)ethan-1-ol was obtained in the form of a colorless solid.

Yield: 77% of theory. M.p.: 173° C.

$^1$H NMR (DMSO-D$_6$, 200 MHz): δ=3.21 (q, J=5.5 Hz, 2H), 3.45 (q, J=5.7 Hz, 2H), 3.70 (s, 3H), 4.71 (t, J=5.38 Hz, 1H), 5.66 (s, 1H), 6.74 (s, 1H), 6.87 (d, J=8.99 Hz, 2H), 7.32 (d, J=9.19 Hz, 2H), 8.00 (s, 1H), 8.63 (s, 1H).

$^{13}$C NMR (DMSO-D$_6$, 50 MHz): δ=42.9 (t), 55.1 (q), 59.9 (t), 113.9 (s), 121.8 (d), 133.4 (d), 154.3 (s), 157.5 (d), 160.3 (d) 162.7 (s).

Combustion Analysis: Calcd. C, 59.99; H, 6.20; N, 21.52. Found C, 59.68; H, 6.00; N, 21.11.

EXAMPLE 2

3-(6-(4-Methoxyphenylamino)pyrimidine-4-ylamino)propan-1-ol

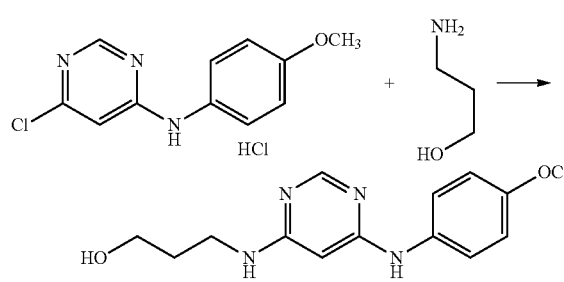

was obtained analogously to the method as set out in Example 1b, but using 75 mg of propanolamine instead of 62 mg of ethanolamine. 3-(6-(4-Methoxyphenylamino)pyrimidine-4-ylamino)propan-1-ol was obtained in the form of a colorless solid.

Yield: 85% of theory. M.p.: 151-152° C.

$^1$H NMR (DMSO-D$_6$, 200 MHz): δ=1.62 (m, 2H), 3.19 (q, J=6.1 Hz, 2H), 3.44 (q, J=5.6 Hz, 2H), 3.71 (s, 3H,), 4.48 (t, J=5.2 Hz, 1H), 5.62 (s, 1H), 6.72 (t, J=5.37 Hz, 1H), 6.86 (d, J=8.9 Hz, 2H), 7.35 (d, J=8.8 Hz, 2H), 8.11 (s, 1H), 8.69 (s, 1H).

$^{13}$C NMR (DMSO-D$_6$, 200 MHz): δ=32.6 (t), 37.5 (t), 55.3 (q), 58.5 (t), 114.1 (4), 122.0 (d), 133.4 (s), 154.5 (s), 157.5 (d), 160.5 (s), 162.7 (s).

Combustion Analysis: Calcd. C, 61.30; H, 6.61; N, 19.42. Found C, 61.17; H, 6.67; N, 19.39.

EXAMPLE 3

N$^4$-Cyclohexyl-N$^6$-(4-methoxyphenyl)pyrimidine-4,6-diamine

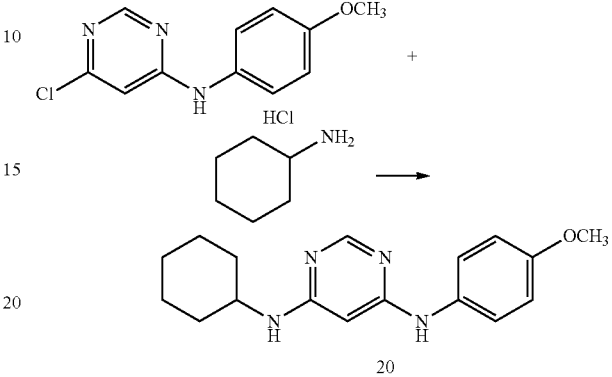

200 mg of 6-chloro-N-(4-methoxyphenyl)pyrimidine-4-amine in the form of a hydrochloride, 80 mg of cyclohexylamine and 109 mg of DIPEA were dissolved in 2 mL of n-BuOH (2 mL) and the mixture obtained was charged into a microwave vial and the vial obtained was heated to 200° C. for 90 minutes under microwave irradiation. Progress of the reaction was monitored by TLC. Upon termination of the reaction n-BuOH was evaporated. The evaporation residue was subjected to MPLC (silica, PE:EtOAc=1:3).

N$^4$-Cyclohexyl-N$^6$-(4-methoxyphenyl)pyrimidine-4,6-diamine was obtained in the form of a colorless solid.

Yield: 70% of theory. M.p.: 218-219° C.

$^1$H NMR (CDCl$_3$, 200 MHz): δ=1.05-2.01 (m, 11H), 3.42 (s, 1H), 3.85 (s, 3H), 4.69 (d, 1H, J=6.5 Hz), 5.49 (s, 1H), 6.68 (s, 1H), 6.93 (d, J=8.9 Hz, 2H), 7.16 (d, J=8.9 Hz, 2H), 8.13 (s, 1H).

$^{13}$C NMR (CDCl$_3$, 50 MHz): δ=24.7 (t), 25.7 (t), 33.0 (t), 49.6 (q/d), 55.6 (q/d), 114.8 (d), 125.3 (d), 131.7 (s), 156.9 (s), 158.4 (d), 161.8 (S), 162.2 (s).

HR-MS: Predicted [MH]$^+$=299.1866; Measured [MH]$^+$=299.1878.

EXAMPLE 4

2-(6-(4-Morpholinophenylamino)pyrimidin-4-ylamino)ethan-1-ol 4a. 6-Chloro-N-(4-morpholinophenyl)pyrimidin-4-amine

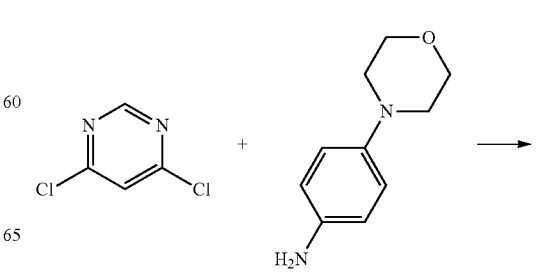

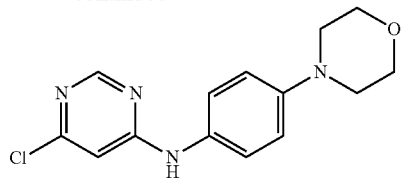

100 mg of 4,6-dichloropyrimidine and 92 mg of p-morpholino aniline were dissolved in 5 mL of i-PrOH. The mixture obtained was refluxed at 84° C. for 6 hours under a nitrogen atmosphere. A colorless precipitate was formed which was collected by filtration. 6-Chloro-N-(4-morpholinophenyl)pyrimidin-4-amine was obtained in the form of a colorless solid.

Yield: 46% of theory. M.p.: 165-166° C.

$^1$H NMR(CH$_3$OD, 200 MHz): δ=3.59 (t, J=4.8 Hz, 4H), 3.99 (t, J=4.8 Hz, 4H), 6.75 (s, 1H), 7.53 (d, J=9.2 Hz, 2H), 7.81 (d, J=9.19 Hz, 2H), 8.38 (s, 1H).

$^{13}$C NMR(CH$_3$OD, 50 MHz): δ=53.5 (t), 63.1 (t), 104.6 (d), 119.8 (d), 120.3 (d), 156.4 (s), 156.9 (s), 160.3 (d).

4b. 2-(6-(4-Morpholinophenylamino)pyrimidin-4-ylamino)ethan-1-ol

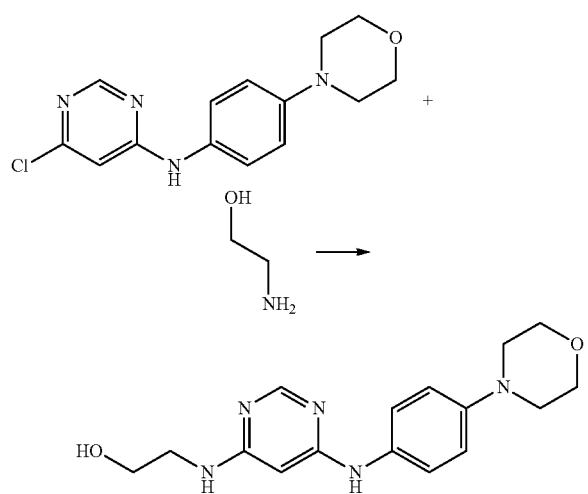

78 mg of 6-chloro-N-(4-morpholinophenyl)pyrimidin-4-amine, 33 mg of ethanolamine and 70 mg of DIPEA were dissolved in 2 mL of n-BuOH and the mixture obtained was charged into a microwave vial and the vial obtained was heated to 200° C. for 60 minutes under microwave irradiation. Progress of the reaction was monitored by TLC. Upon termination of the reaction n-BuOH. was evaporated off and the evaporation residue obtained was subjected to crystallization from n-BuOH-EtOH solvent mixture. 2-(6-(4-Morpholinophenylamino)pyrimidin-4-ylamino)ethan-1-ol was obtained in the form of a colorless solid.

Yield: 77% of theory. M.p.: 204-207° C.

$^1$H NMR(CH$_3$OD, 200 MHz): δ=3.11 (t, J=4.69 Hz, 4H), 3.36 (m, 2H), 3.66 (t, J=5.7 Hz, 2H), 3.84 (t, J=4.5 Hz, 4H), 5.69 (s, 1H), 6.97 (d, J=8.8 Hz, 2H), 7.22 (d, J=8.9 Hz, 2H) 7.89 (s, 1H).

$^{13}$C NMR(CH$_3$OD, 50 MHz): δ=44.5 (t), 51.0 (t), 61.8 (t), 68.9 (t), 82.9 (d), 117.9 (d), 125.4 (d), 133.3 (s), 137.7 (s), 149.9 (s), 158.4 (d), 164.2 (s).

HR-MS: Predicted [MH]$^+$=316.1768; Measured [MH]$^+$=316.1760.

EXAMPLE 5

N$^4$-Cyclohexyl-N$^6$-(4-morpholinophenyl)pyrimidine-4,6-diamine 78 mg of 6-chloro-N-(4-morpholinophenyl)pyrimidin-4-amine, 55 mg of cyclohexylamine and 72 mg if DIPEA were dissolved in 2 mL of n-BuOH and the mixture obtained was charged into a microwave vial and the vial obtained was heated to 200° C. for 90 minutes under microwave irradiation. Upon evaporation of n-BuOH a precipitate formed and was subjected to crystallization from n-BuOH-EtOH solvent mixture. N$^4$-Cyclohexyl-N$^6$-(4-morpholinophenyl)pyrimidine-4,6-diamine was obtained in the form of a colorless solid.

Yield: 44% of theory. M.p.: 239-240° C.

$^1$H NMR (DMSO-D$_6$, 200 MHz): δ=0.98-1.90 (m, 11H), 3.01 (t, J=4.5 Hz 4H), 3.72 (t, J=4.2 Hz, 4H), 5.61 (s, 1H), 6.61 (d, J=8.0 Hz, 1H), 6.87 (d, J=8.6 Hz, 2H), 7.27 (d, J=8.8 Hz, 2H), 7.98 (s, 1H), 8.51 (s, 1H).

$^{13}$C NMR(CH$_3$OD, 50 MHz): δ=24.8 (t), 25.2 (t), 32.8 (t), 48.5 (d), 49.3 (t), 66.5 (t), 82.6 (d), 115.8 (d), 121.9 (d), 132.8 (s), 146.6 (s), 157.6 (d), 160.5 (s), 161.9 (s).

HR-MS: Predicted [MH]$^+$=354.2288; Measured [MH]$^+$=354.2288.

EXAMPLE 6

3-(6-(4-Morpholinophenylamino)pyrimidin-4-ylamino)propan-1-ol

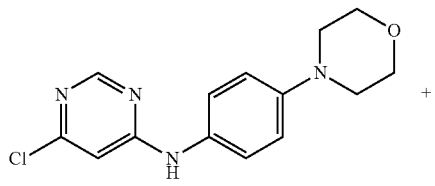

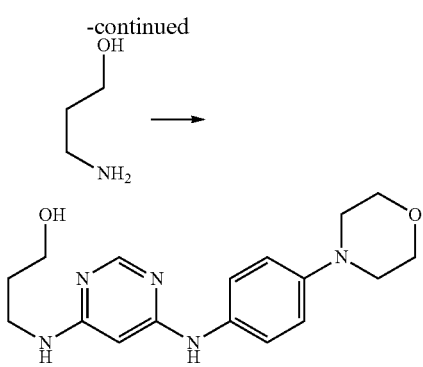

165 mg of 6-chloro-N-(4-morpholinophenyl)pyrimidin-4-amine, 86 mg of propanolamine and 147 mg of DIPEA were dissolved in 2 mL of n-BuOH, The mixture obtained was charged into a microwave vial and the vial obtained was heated to 200° C. for 60 minutes under microwave irradiation. n-BuOH was evaporated off and the evaporation residue was subjected to crystallization from n-BuOH-EtOH solvent mixture. 3-(6-(4-Morpholinophenylamino)pyrimidin-4-ylamino)propan-1-ol was obtained in the form of a colorless solid.

Yield: 40% of theory. M.p.: 198-199° C.

$^1$H NMR (DMSO-D$_6$, 200 MHz): δ=1.56-1.71 (m, 2H), 3.01 (t, J=4.2 Hz, 4H), 3.19 (s, 2H), 3.43 (t, J=5.3 Hz, 2H), 3.72 (t, J=4.1 Hz, 4H), 4.47 (t, J=4.6 Hz, 1H), 5.62 (s, 1H), 6.71 (t, J=4.5 Hz, 1H), 6.87 (d, J=8.9 Hz, 2H), 7.29 (d, J=7.2 Hz, 2H), 7.99 (s, 1H), 8.57 (s, 1H).

$^{13}$C NMR(CH$_3$OD, 50 MHz): δ=32.2 (q), 37.4 (t), 49.3 (t), 58.3 (t), 66:3 (t), 82.2 (d), 115.9 (d), 121.9 (d), 132.8 (d), 146.4 (s), 157.7 (d), 160.5 (s), 162.7 (s).

HR-MS: Predicted [MH]$^+$=330.1925; Measured [MH]$^+$=330.1937.

EXAMPLE 7

2-(6-(4-(Phenylamino)phenylamino)pyrimidin-4-ylamino)ethan-1-ol

7a. N$^1$-(6-Chloropyrimidin-4-yl)-N$^4$-phenylbenzene-1,4-diamine

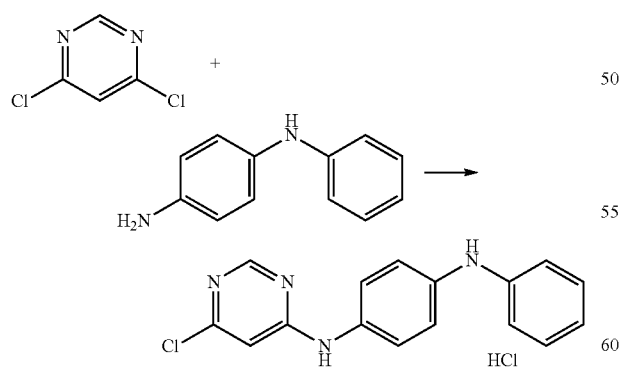

200 mg of 4,6-dichloropyrimidine and 190 mg of 4-aminodiphenyamine were dissolved in 5 mL of i-PrOH and to the mixture obtained 0.3 mL of 37% HCl were added. The mixture obtained was refluxed at 84° C. for 4 hours under a nitrogen atmosphere. A light yellow precipitate was formed which was collected by filtration. N$^1$-(6-chloropyrimidin-4-yl)-N$^4$-phenylbenzene-1,4-diamine in the form of a hydrochloride was obtained in the form of a light yellow solid.

Yield: 45% of theory.

$^1$H NMR (DMSO-D$_6$, 200 MHz): δ=3.8 (s, 1H), 6.8 (s, 2H), 7.1 (t, J=8.99 Hz, 4H), 7.3 (t, J=7.43 Hz, 2H), 7.5 (d, J=7.62 Hz, 2H), 7.9 (s, 1H), 8.5 (s, 1H), 10.0 (s, 1H).

$^{13}$C NMR (DMSO-D$_6$, 50 MHz): δ=104.1 (d), 116.1 (d), 117.9 (d), 119.1 (d), 122.4 (d), 129.2 (d), 133.2 (s), 143.9 (s), 150.1 (s), 157.3 (s), 158.9 (d), 161.1 (s).

7b. 2-(6-(4-(Phenylamino)phenylamino)pyrimidin-4-ylamino)ethan-1-ol 176 mg of N$^1$-(6-chloropyrimidin-4-yl)-N$^4$-phenylbenzene-1,4-diamine in the form of a hydrochloride, 72 mg of ethanolamine and 153 mg of DIPEA were dissolved in 2 mL of n-BuOH and the mixture obtained was charged into a microwave vial and the vial obtained was heated to 200° C. for 60 minutes under microwave irradiation. Progress of the reaction was monitored by TLC. Upon termination of the reaction n-BuOH was evaporated and the evaporation residue was subjected to MPLC eluting the product with EtOAc. 2-(6-(4-(Phenylamino)phenylamino)pyrimidin-4-ylamino)ethan-1-ol was obtained in the form of a solid.

Yield: 32% of theory. M.p.: 154-155° C.

$^1$H NMR (CD$_3$OD, 200 MHz): δ=3.24-3.27 (m, 4H), 3.61 (t, J=5.6 Hz, 2H), 5.64 (s, 1H), 6.95-7.07 (m, 4H), 7.08-7.21 (m, 4H), 7.92 (s, 1H).

$^{13}$C NMR (CD$_3$OD, 50 MHz): δ=43.8 (t), 60.9 (t), 82.3 (d), 117.4 (d), 118.6 (d) 120.4 (d), 124.9 (d), 129.3 (d), 132.1 (s), 141.5 (s), 144.7 (s), 157.8 (d), 162.0 (s), 163.6 (s).

HR-MS: Predicted [MH]$^+$=322.1662; Measured [MH]$^+$=322.1674.

EXAMPLE 8

2-(6-(4-Phenoxyphenylamino)pyrimidin-4-ylamino)ethan-1-ol 8a. 6-Chloro-N-(4-phenoxyphenyl)pyrimidin-4-amine

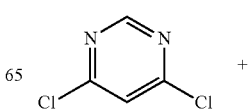

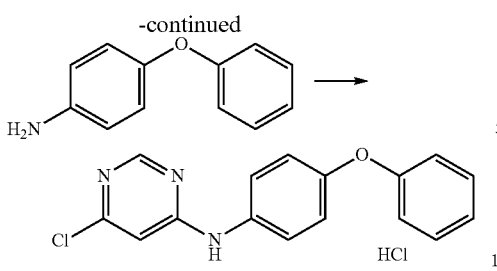

200 mg of 4,6-Dichloropyrimidine and 191 mg of 4-aminodiphenylamine were dissolved in 5 mL of i-PrOH and to the mixture obtained 0.3 mL of 37% HCl were added. The mixture obtained was refluxed at 84° C. for 4 hours under a nitrogen atmosphere and a brown-red precipitate was formed and was collected by filtration. 6-Chloro-N-(4-phenoxyphenyl)pyrimidin-4-amine on the form of a hydrochloride was obtained in the form of a red-brown solid.

Yield: 50% of theory.

$^1$H NMR (DMSO-D$_6$, 200 MHz): δ=6.9 (s, 2H), 7.0 (m, 5H), 7.4 (t, J=7.7 Hz, 2H), 7.6 (d, J=8.9 Hz, 2H), 8.4 (s, 1H), 10.3 (s, 1H), 10.8 (s, 1H).

$^{13}$C NMR (DMSO-D$_6$, 50 MHz): δ=104.9 (d), 117.9 (d) 119.4 (d) 122.2 (d), 122.8 (d), 130.0 (d), 134.8 (s), 144.8 (s), 151.9 (s), 157.1 (s), 158.3 (d), 161.3 (s).

8b. 2-(6-(4-Phenoxyphenylamino)pyrimidin-4-ylamino)ethan-1-ol

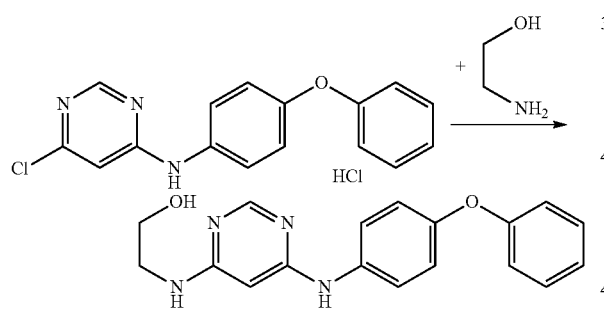

225 mg of 6-chloro-N-(4-phenoxyphenyl)pyrimidin-4-amine, 82 mg of ethanolamine and 173 mg of DIPEA were dissolved in 2 mL of n-BuOH and the mixture obtained was charged into a microwave vial and the vial obtained was heated to 200° C. for 60 minutes under microwave irradiation. Progress of the reaction was monitored by TLC. Upon termination of the reaction n-BuOH was evaporated and the evaporation residue was subjected to MPLC purification (EtOAc: EtOH=10:1). 2-(6-(4-Phenoxyphenylamino)pyrimidin-4-ylamino)ethan-1-ol was obtained in the form of a colorless solid.

Yield: 60% of theory. M.p.: 154-156° C.

$^1$H NMR (DMSO-D$_6$, 200 MHz): δ=3.19-3.30 (m, 2H), 3.49 (q, J=5.7 Hz, 2H), 4.73 (t, J=5.2 Hz, t), 5.77 (s, 1H), 6.73-7.13 (m, 6H), 7.35 (t, J=8.8 Hz, 2H), 7.53 (d, J=8.7 Hz, 2H), 8.07 (s, 1H), 8.90 (s, 1H).

$^{13}$C NMR (DMSO-D$_6$, 50 MHz): δ=42.9 (t), 60.7 (t), 83.0 (d), 117.4 (d), 119.9 (d) 121.2 (d), 122.7 (d), 130.03 (d), 131.9 (s), 141.2 (s), 144.2 (s), 157.3 (d), 161.9 (s), 163.8 (s).

Combustion Analysis: Calcd. C, 67.07; H, 5.63; N, 17.38. Found C, 67.11; H, 5.48; N, 17.00.

EXAMPLE 9

$N^4$-(4-Methoxyphenyl)-$N^6$-propylpyrimidine-4,6-diamine

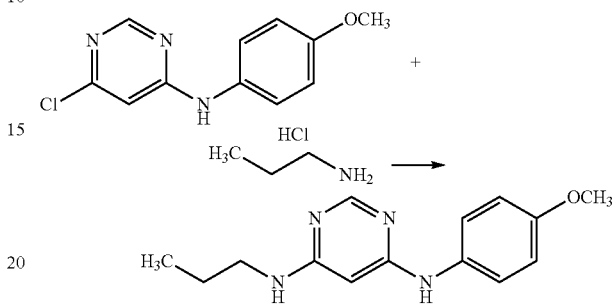

100 mg of 6-chloro-N-(4-methoxyphenyl)pyrimidine-4-amine in the form of a hydrochloride, 66 mg of propylamine and 120 mg of DIPEA were dissolved in 1 mL of n-BuOH and the mixture obtained was charged into a microwave vial and the vial obtained was heated to 200° C. for 60 minutes under microwave irradiation. Progress of the reaction was monitored by TLC. Upon termination of the reaction n-BuOH was evaporated off and the evaporation residue was subjected to crystallization from n-BuOH-EtOH solvent mixture. $N^4$-(4-Methoxyphenyl)-$N^6$-propylpyrimidine-4,6-diamine was obtained in the form of a colorless solid.

Yield: 82% of theory. M.p.: 194-196° C.

$^1$H NMR CDCl$_3$, 200 MHz): δ=0.95 (t, J=7.7 Hz, 3H), 1.51-1.67 (m, 2H), 3.09 (q, J=6.9 Hz, 2H), 3.83 (s, 3H), 4.81 (s, 1H), 5.49 (s, 1H), 6.65 (s, 1H), 6.90 (d, J=8.2 Hz, 2H), 7.19 (d, J=8.6 Hz, 2H), 8.13 (s, 1H).

$^{13}$C NMR (CDCl$_3$, 50 MHz): δ=115 (q), 22.5 (d), 43.3 (d), 55.6 (q), 80.3 (d), 114.8 (d), 125.8 (d), 131.3 (s), 157.0 (s), 158.2 (d), 162.0 (s), 163.2 (s).

Combustion Analysis: Calcd. C, 65.09; H, 7.02; N, 21.69. Found C, 65.14; H, 6.79; N, 21.43.

EXAMPLE 10

$N^4$-Ethyl-$N^6$-(4-methoxyphenyl)pyrimidine-4,6-diamine

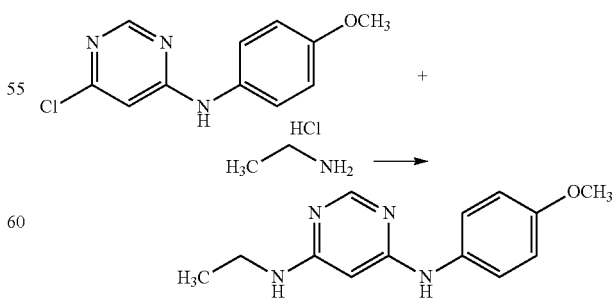

$N^4$-Ethyl-$N^6$-(4-methoxyphenyl)pyrimidine-4,6-diamine was obtained analogously to the method of Example 9, but using 83 mg of ethylamine instead of 66 mg of propylamine and microwave irridation treatment for 45 minutes instead of 60 minutes. $N^4$-Ethyl-$N^6$-(4-methoxyphenyl)pyrimidine-4,6-diamine was obtained in the form of a colorless solid.

Yield: 71% of theory. M.p.: 190-193° C.

$^1$H NMR CDCl$_3$, 200 MHz): δ=1.20 (t, J=6.8 Hz, 3H), 3.07-3.3.25 (m, 2H), 3.82 (s, 3H), 4.87 (s, 1H), 5.49 (s, 1H), 6.91 (d, J=8.6 Hz, 2H), 7.19 (d, J=8.6 Hz, 2H), 8.12 (s, 1H).

$^{13}$C $^{13}$C NMR (CDCl$_3$, 50 MHz): δ=14.3 (q), 36.3 (t), 55.4 (q), 80.3 (d), 114.6 (d), 125.5 (d), 131.3 (s), 157.0 (s), 158.2 (d), 162.0 (s), 163.0 (s).

Combustion Analysis: Calcd. C, 63.91; H, 6.60; N, 22.93. Found C, 63.68; H, 6.43; N, 22.59.

EXAMPLE 11

$N^4$-(4-Methoxyphenyl)-$N^6$-methylpyrimidine-4,6-diamine

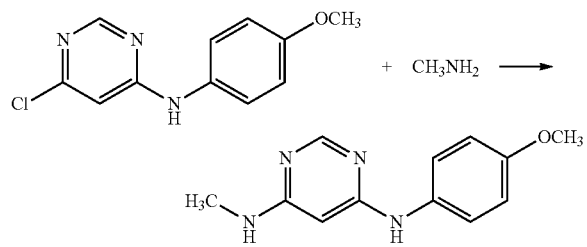

100 mg of 6-chloro-N-(4-methoxyphenyl)pyrimidine-4-amine in the form of a hydrochloride, 57 mg of methylamine and 238 mg of DIPEA were dissolved in 1 mL of n-BuOH in a screw cap vial and the mixture obtained was heated to 120° C. for 1 hour. Progress of the reaction was monitored by TLC. Upon termination of the reaction n-BuOH. was evaporated off and the evaporation residue was subjected to crystallization from n-BuOH/EtOH solvent mixture. $N^4$-(4-Methoxyphenyl)-$N^6$-methylpyrimidine-4,6-diamine was obtained in the form of a light yellow solid.

Yield: 91% of theory. M.p.: 174-182° C.

$^1$H NMR (DMSO-D$_6$, 200 MHz): δ=2.70 (d, J=4.7 Hz, 3H), 3.72 (s, 3H), 5.58 (s, 1H), 6.71 (d, J=4.7 Hz, 1H), 6.87 (d, J=9.2 Hz, 2H), 7.37 (d, J=8.8 Hz, 2H), 8.02 (s, 1H), 8.67 (s, 1H).

$^{13}$C NMR (DMSO-D$_6$, 50 MHz): δ=27.4 (q), 55.1 (q), 81.9 (d), 113.8 (d), 121.8 (d), 133.6 (s), 154.3 (s), 157.5 (d), 160.5 (s), 163.1 (s).

HR-MS: Predicted [MH]$^+$=231.1240; Measured [MH]$^+$=231.1242.

EXAMPLE 12

$N^4$-(2-Propyl)-$N^6$-(4-methoxyphenyl)pyrimidine-4,6-diamine

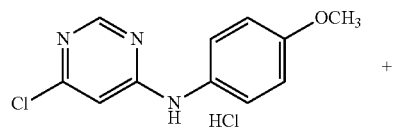

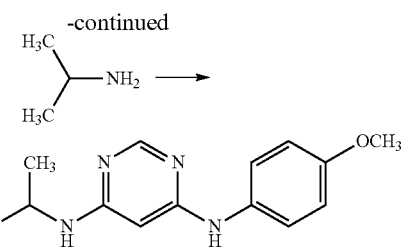

100 mg of 6-chloro-N-(4-methoxyphenyl)pyrimidine-4-amine in the form of a hydrochloride, 44 mg of isopropylamine and 95 mg of DIPEA were dissolved in 1 mL of n-BuOH in a screw cap vial and the vial obtained was heated to 120° C. for 1 hour. Progress of the reaction was monitored by TLC. Upon termination of the reaction n-BuOH was evaporated off and the evaporation residue obtained was subjected to flash column chromatography (PE:EtOAc 1:1). $N^4$-Isopropyl-$N^6$-(4-methoxyphenyl)pyrimidine-4,6-diamine was obtained in the form of a colorless solid.

Yield: 73% of theory. M.p.: 180-182° C.

$^1$H NMR (DMSO-D$_6$, 200 MHz): δ=1.08-1.11 (d, J=6.5 Hz, 7H), 3.70 (s, 3H), 5.60 (s, 1H), 6.61 (d, J=7.8 Hz, 1H), 6.85 (d, J=8.8 Hz, 2H) 7.34 (d, J=8.9 Hz, 2H), 8.01 (s, 1H), 8.59 (s, 1H).

$^{13}$C NMR (DMSO-D$_6$, 50 MHz): δ=22.6 (q), 41.3 (d), 55.3 (q), 82.8 (d), 114.1 (d), 122.3 (d), 133.6 (s), 154.5 (s), 157.7 (d), 160.5 (s), 161.9 (s).

HR-MS: Predicted [MH]$^+$=259.1553; Measured [MH]$^+$=259.1552.

EXAMPLE 13

$N^4$-(2-Methoxyethyl)-$N^6$-(4-methoxyphenyl)pyrimidine-4,6-diamine

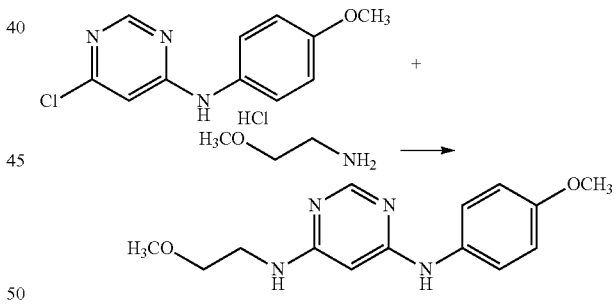

75 mg of 6-chloro-N-(4-methoxyphenyl)pyrimidine-4-amine in the form of a hydrochloride, 23 mg of 2-methoxyethanamine and 90 mg of DIPEA were dissolved in 1 mL of n-BuOH and charged into a microwave vial and the vial obtained was heated to 200° C. for 45 minutes under microwave irradiation. The reaction was monitored by TLC. The crude product was obtained by evaporating n-BuOH. Purification was carried out by column chromatography using EtOAc:EtOH:NEt$_3$=10:1:0.5 solvent mixture. $N^4$-(2-Methoxyethyl)-$N^6$-(4-methoxyphenyl)pyrimidine-4,6-diamine in the form of a colorless solid was obtained.

Yield: 71% of theory.

$^1$H NMR (CDCl$_3$, 200 MHz): δ=3.34 (s, 3H), 3.38 (t J=4.9 Hz, 2H), 3.44-3.55 (m, 2H), 3.81 (s, 3H), 5.15 (s, 1H), 5.53 (s, 1H), 6.89 (d, J=8.8 Hz, 2H), 7.17 (d, J=8.8 Hz, 2H), 8.14 (s, 1H).

$^{13}$C NMR (CDCl$_3$, 50 MHz): δ=40.9 (t), 55.5 (q), 58.8 (q), 80.9 (d), 114.6 (d), 125.4 (d), 131.7 (s), 156.9 (s), 158.2 (d), 162.1 (s), 163.1 (s).

EXAMPLE 14

2-(6-(4-Methoxyphenylamino)pyrimidin-4-ylamino)acetic acid

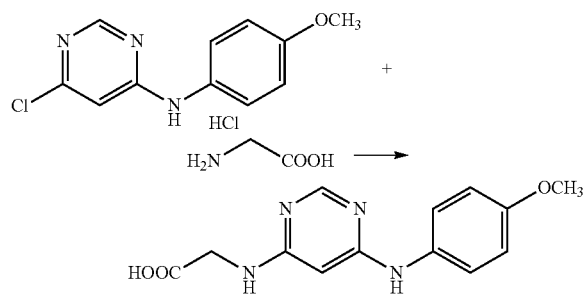

45 mg of 6-chloro-N-(4-methoxyphenyl)pyrimidine-4-amine in the form of a hydrochloride, 14 mg of 2-aminoacetic acid and 56 mg of DIPEA were dissolved in 1 mL of n- and charged into a microwave vial and the vial obtained was heated to 200° C. for 45 minutes under microwave irradiation. The reaction was monitored by TLC. The crude product was obtained by evaporating n-BuOH. Purification was carried out by column chromatography using EtOAc: NEt$_3$=50:1 solvent mixture. 2-(6-(4-Methoxyphenylamino)pyrimidin-4-ylamino)acetic acid in the form of a colorless solid was obtained.

Yield: 60% of theory.

$^1$H NMR (DMSO-D$_6$, 200 MHz): δ=2.68 (s, 2H), 3.71 (s, 3H), 5.59 (s, 1H), 6.70 (d, J=4.7 Hz, 1H), 6.86 (d, J=8.8 Hz, 2H), 7.37 (d, J=8.9 Hz, 2H), 8.02 (s, 1H), 8.67 (s, 1H).

$^{13}$C NMR (DMSO-D$_6$, 50 MHz): δ=27.2 (t), 55.1 (q), 81.9 (d), 114.1 (d), 122.3 (d), 133.5 (s), 154.5 (s), 157.1 (d), 160.4 (s), 162.9 (s).

EXAMPLE 15

N-(4-Methoxyphenyl)-6-morpholinopyrimidin-4-amine

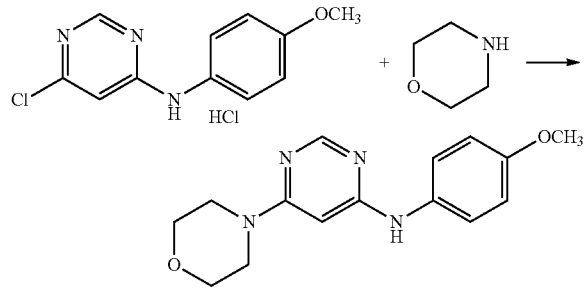

50 mg of 6-chloro-N-(4-methoxyphenyl)pyrimidine-4-amine in the form of a hydrochloride, 17 mg of morpholine and 64 mg of DIPEA were dissolved in 1 mL of n-BuOH and charged into a microwave vial and the vial obtained was heated to 200° C. for 30 minutes under microwave irradiation. The reaction was monitored by TLC. The crude product was obtained by evaporating n-BuOH. Purification was carried out by column chromatography using EtOAc. N-(4-Methoxyphenyl)-6-morpholinopyrimidin-4-amine in the form of a colorless solid was obtained.

Yield: 89% of theory.

$^1$H NMR (CDCl$_3$, 200 MHz): δ=3.46 (t, J=4.6 Hz, 4H), 3.73 (t, J=4.9 Hz, 4H), 3.82 (s, 3H), 5.68 (s, 1H), 6.91 (d, J=8.9 Hz, 2H), 7.20 (d, J=8.8 Hz, 2H), 7.48 (bs, 1H), 8.21 (s, 1H). $^{13}$C NMR (CDCl$_3$, 50 MHz): δ=44.3 (t), 55.5 (q), 66.5 (t), 81.0 (d), 114.7 (d), 125.6 (d), 131.4 (s), 157.1 (s), 157.9 (d), 162.6 (s), 163.2 (s).

EXAMPLE 16

2-((6-(4-Methoxyphenylamino)pyrimidin-4-yl)(methyl)amino)ethan-1-ol

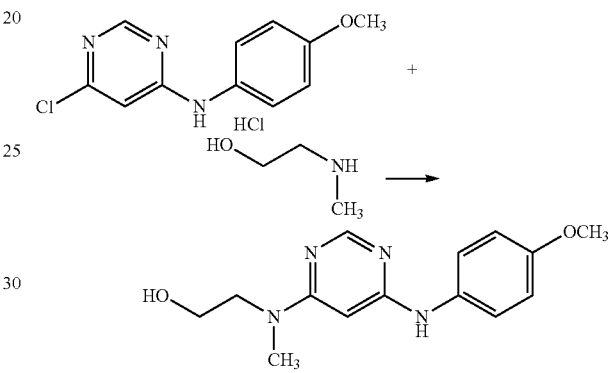

75 mg of 6-chloro-N-(4-methoxyphenyl)pyrimidine-4-amine in the form of a hydrochloride, 23 mg of 2-(methylamino)ethanol and 90 mg of DIPEA were dissolved in 1 mL of n-BuOH and charged into a microwave vial and the vial obtained was heated to 200° C. for 30 minutes under microwave irradiation. The reaction was monitored by TLC. The crude product was obtained by evaporating n-BuOH. Purification was carried out by column chromatography using EtOAc. 2-((6-(4-Methoxyphenylamino)pyrimidin-4-yl)(methyl)amino)ethan-1-ol in the form of a colorless solid was obtained.

Yield: 89% of theory.

$^1$H NMR (CDCl$_3$, 200 MHz): δ=2.90 (s, 3H), 3.60-3.70 (m, 2H), 3.71-3.78 (m, 2H), 3.80 (s, 3H), 4.55 (bs, 1H), 5.58 (s, 1H), 6.88 (d, J=8.8 Hz, 2 h), 7.18 (d, J=8.9 Hz, 2H), 7.71 (s, 1H), 8.07 (s, 1H).

$^{13}$C NMR (CDCl$_3$, 50 MHz): δ=37.1 (t), 53.2 (q), 55.5 (t), 62.2 (q), 80.6 (d), 114.7 (d), 125.4 (d), 131.9 (s), 157.0 (s), 157.2 (d), 161.9 (s), 163.1 (s).

EXAMPLE 17

N$^4$-Butyl-N$^6$-(4-methoxyphenyl)pyrimidine-4,6-diamine

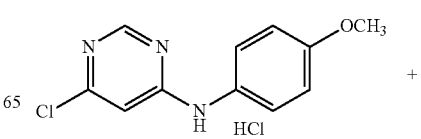

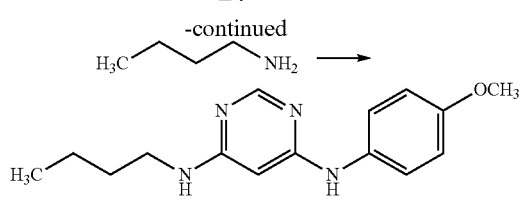

75 mg of 6-chloro-N-(4-methoxyphenyl)pyrimidine-4-amine in the form of a hydrochloride, 23 mg of butan-1-amine and 90 mg of DIPEA were dissolved in 1 mL of n-BuOH and charged into a microwave vial and the vial obtained was heated to 200° C. for 45 minutes under microwave irradiation. The reaction was monitored by TLC. The crude product was obtained by evaporating n-BuOH. Purification was carried out by column chromatography using EtOAc. $N^4$-Butyl-$N^6$-(4-methoxyphenyl)pyrimidine-4,6-diamine in the form of a colorless solid was obtained.

Yield: 81% of theory.

$^1$H NMR (CDCl$_3$, 200 MHz): δ=0.90 (t J=7.1 Hz, 3H), 1.19-1.43 (m, 2H), 1.43-1.64 (m, 2H), 3.08 (dd, J$_1$=12.1 Hz, J$_2$=5.8 Hz, 2H), 3.81 (s, 3H), 5.24 9bs, 1H), 5.50 (s, 1H), 6.90 (d, J=8.8 Hz, 2H), 7.18 (d, J=8.9 Hz, 2H), 7.71 (s, 1H), 8.08 (s, 1H).

$^{13}$C NMR (CDCl$_3$, 50 MHz): δ=13.8 (q), 20.1 (t), 31.2 (t), 41.2 (t), 55.5 (q), 80.0 (d), 114.6 (d), 125.4 (d), 131.7 (s), 156.9 (s), 158.0 (d), 162.1 (s), 163.1 (s).

EXAMPLE 18

$N^4$-Cyclopentyl-$N^6$-(4-methoxyphenyl)pyrimidine-4,6-diamine

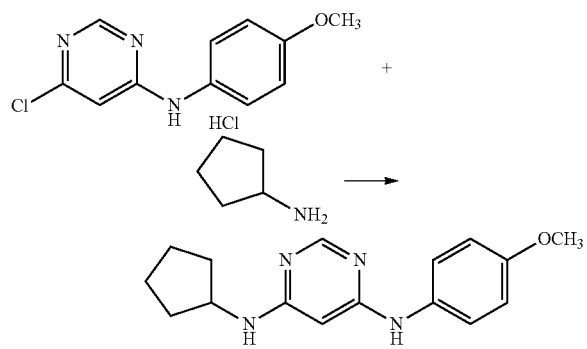

75 mg of 6-chloro-N-(4-methoxyphenyl)pyrimidine-4-amine in the form of a hydrochloride, 26 mg of cyclopentylamine and 90 mg of DIPEA were dissolved in 1 mL of n-BuOH and charged into a microwave vial and the vial obtained was heated to 200° C. for 45 minutes under microwave irradiation. The reaction was monitored by TLC. The crude product was obtained by evaporating n-BuOH. Purification was carried out by column chromatography using EtOAc. $N^4$-Cyclopentyl-$N^6$-(4-methoxyphenyl)pyrimidine-4,6-diamine in the form of a colorless solid was obtained.

Yield: 83% of theory.

$^1$H NMR (DMSO-D$_6$, 200 MHz): δ=1.25-1.96 (m, 8H), 3.71 (s, 3H), 3.88-4.05 (bs, 1H), 5.62 (s, 1 h), 6.74 (d, J=6.9 Hz, 1H), 6.86 (d, J=8.9 Hz, 2H), 7.35 (d, J=8.8 Hz, 2H), 8.00 (s, 1H), 8.61 (s, 1H).

$^1$H NMR (DMSO-D$_6$, 50 MHz): δ=23.4 (t), 32.3 (t), 51.7 (d), 55.7 (q), 82.6 (d), 113.9 (d), 122.1 (d), 133.6 (s), 154.5 (s), 157.5 (d), 160.4 (s), 162.2 (s).

EXAMPLE 19

$N^4$-sec-Butyl-$N^6$-(4-methoxyphenyl)pyrimidine-4,6-diamine

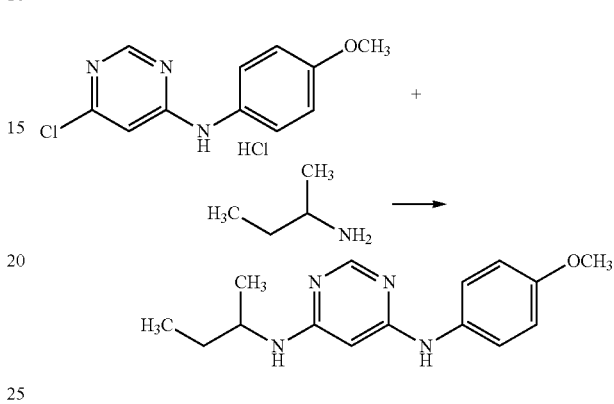

75 mg of 6-chloro-N-(4-methoxyphenyl)pyrimidine-4-amine in the form of a hydrochloride, 22 mg of butan-2-amine and 90 mg of DIPEA were dissolved in 1 mL of n-BuOH and charged into a microwave vial and the vial obtained was heated to 200° C. for 45 minutes under microwave irradiation. The reaction was monitored by TLC. The crude product was obtained by evaporating n-BuOH. Purification was carried out by column chromatography using EtOAc. $N^4$-sec-Butyl-$N^6$-(4-methoxyphenyl)pyrimidine-4,6-diamine in the form of a colorless solid was obtained.

Yield: 38% of theory $^1$H NMR (CDCl$_3$, 200 MHz): δ=0.89 (t, J=7.4 Hz, 3H), 1.12 (d, J=6.5 Hz, 3H), 1.48 (m, 2H), 3.34-3.59 (m, 1H), 3.81 (s, 3H), 4.96 (d, J=7.82 Hz, 1H), 5.49 (s, 1H), 6.89 (d, J=8.8 Hz, 2H), 7.18 (d, J=8.2 Hz, 2H), 7.57 (s, 1H), 8.08 (s, 1H).

$^{13}$C NMR (CDCl$_3$, 50 MHz): δ=10.3 (q), 20.2 (q), 29.6 (t), 48.1 (q), 55.5 (q), 80.4 (d), 114.6 (d), 125.4 (d), 131.7 (s), 156.9 (s), 158.2 (d), 162.1 (s), 162.6 (s).

EXAMPLE 20

$N^4$-tert-Butyl-$N^6$-(4-methoxyphenyl)pyrimidine-4,6-diamine

20a. N-tert-Butyl-6-chloropyrimidin-4-amine

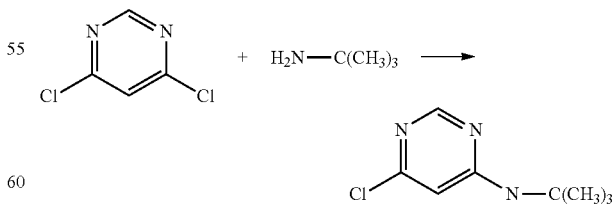

251 mg of 4,6-dichloropyrimidine, 123 mg of 2-methylpropan-2-amine and 260 mg of DIPEA were dissolved in 2.5 mL of i-PrOH and charged into a screw cap vial and the vial obtained was kept overnight in a heating block at 90° C. The reaction was monitored by TLC and was completed after 12 hours. The mixture obtained was cooled to r.t., solvent was evaporated and pure N-tert-butyl-6-chloropyrimidin-4-amine was obtained by column chromatography using PE:EtOAc 10:1.

Yield: 90% of theory.

$^1$H NMR (CDCl$_3$, 200 MHz): δ=1.43 (s, 9H), 4.93-5.19 (bs, 1H), 7.26 (s, 1H), 8.31 (s, 1H).

$^{13}$C NMR (CDCl$_3$, 50 MHz): δ=28.9 (q), 51.8 (s), 103.6 (d), 158.2 (d), 158.9 (s), 162.6 (s).

20b. N$^4$-tert-Butyl-N$^6$-(4-methoxyphenyl)pyrimidine-4,6-diamine

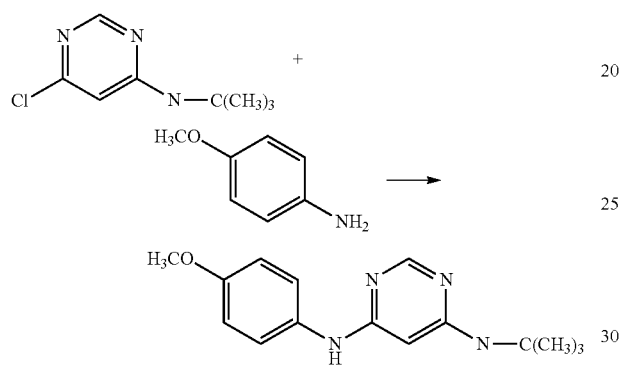

50 mg of N-tert-butyl-6-chloropyrimidin-4-amine, 39 mg of p-anisidine, 104 mg of CsCO$_3$, 1.2 mg of Pd(OAc)$_2$ and 3 mg of BINAP were taken in a screw cap vial under argron in 2 mL of dry toluene and the vial obtained was kept in a heating block at 150° C. for 12 hours. The mixture obtained was cool to r.t. and purification was carried out by column chromatography using 30% EtOAc in PE. N$^4$-tert-Butyl-N$^6$-(4-methoxyphenyl)pyrimidine-4,6-diamine was obtained.

Yield: 48% of theory.

$^1$H NMR (CDCl$_3$, 200 MHz): δ=1.32 (s, 9H), 3.81 (s, 3H), 4.84 (s, 1H), 5.62 (s, 1H), 6.89 (d, J=8.8 Hz, 2H), 7.18 (d, J=8.8 hz, 2H), 7.34-7.54 (bs, 1H), 7.98-8.19 (bs, 1H).

$^{13}$C NMR (CDCl$_3$, 50 MHz): δ=27.5 (q), 48.8 (s), 53.7 (q), 112.8 (d), 123.5 (d), 129.5 (s), 155.1 (s).

EXAMPLE 21

N$^4$-Adamant-1-yl-N$^6$-(4-methoxyphenyl)pyrimidine-4,6-diamine

21a. N-Adamant-1-yl-6-chloropyrimidin-4-amine

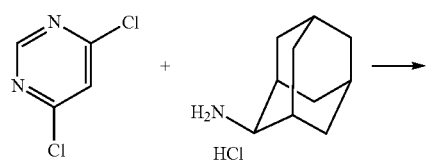

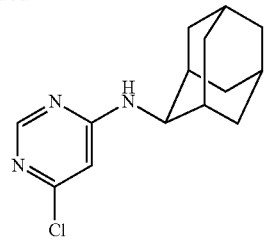

200 mg of 4,6-dichloropyrimidine, 252 mg of 1-aminoadamantane hydrochloride and 452 mg of DIPEA were dissolved in 2 mL of i-PrOH and the mixture obtained was charged into a screw cap vial and the vial was kept overnight in a heating block at 90° C. The reaction was monitored by TLC and was completed after 12 hours. The mixture obtained was cooled to r.t., solvent was evaporated and N-adamant-1-yl-6-chloropyrimidin-4-amine was obtained by column chromatography using PE:EtOAc 10:1.

Yield: 56% yield of theory.

$^1$H NMR (CDCl$_3$, 200 MHz): δ=1.66-1.77 (m, 7H), 1.99-2.08 (m, 6H), 2.09-2.20 9bs, 3H), 4.38-5.03 (bs, 1H), 6.37 (s, 1H), 8.29 (s, 1H).

$^{13}$C NMR (CDCl$_3$, 50 MHz): δ=29.3 (t), 36.2 (d), 41.6 (d), 103.8 (d), 158.2 (d).

21b. N$^4$-Adamant-1-yl-N$^6$-(4-methoxyphenyl)pyrimidine-4,6-diamine

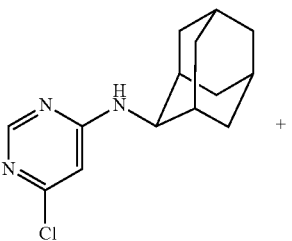

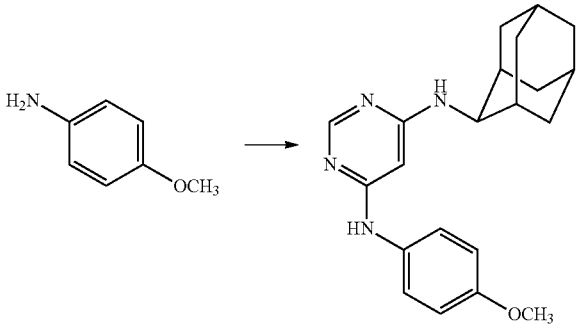

100 mg of N-adamant-1-yl-6-chloropyrimidin-4-amine, 56 mg of p-anisidine, 73 mg of Na-butylate, 2.2 mg of Pd(OAc)$_2$ and 12 mg of BINAP were taken in a screw cap vial under agron in 4 mL of dry toluene and the vial was kept in a heating block at 150° C. for 12 hours. The mixture obtained was cooled to r.t. and purification was carried out by column chromatography using PE:EtOAc 2:1. N$^4$-Adamant-1-yl-N$^6$-(4-methoxyphenyl)pyrimidine-4,6-diamine was obtained.

Yield: 65% of theory.

$^1$H NMR (CDCl$_3$, 200 MHz): δ=1.54-1.77 (m, 6H), 1.88-1.99 (m, 6H), 2.02-2.14 (bs, 3H), 2.20-2.40 (bs, 1H), 3.82 (s,

3H), 4.73 (s, 1H), 5.69 (1H), 6.90 (d, J=8.8 Hz, 2 h), 7.19 (d, J=8.9 Hz, 2H), 7.40 (s, 1H), 8.09 (s, 1H).

$^{13}$C NMR (CDCl$_3$, 50 MHz): δ=29.4 (d), 36.3 (t), 42.1 (t), 51.4 (s), 55.5 (q), 83.2 (d), 114.6 (d), 125.2 (d), 131.7 (s), 156.9 (s), 158.0 (d), 161.3 (s), 161.9 (s).

EXAMPLE 22

2-(6-(3-Methoxyphenylamino)pyrimidin-4-ylamino)ethan-1-ol

22a. 6-Chloro-N-(3-methoxyphenyl)pyrimidin-4-amine

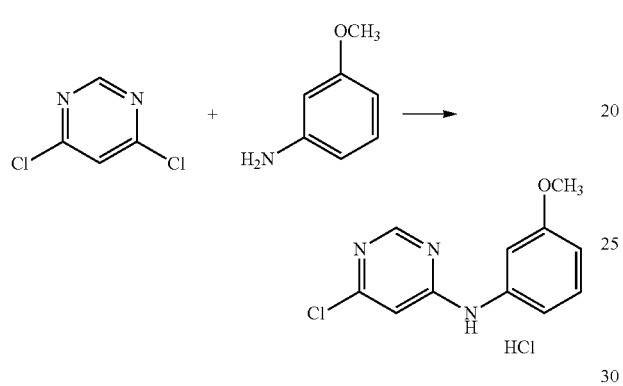

250 mg of 4,6-dichloropyrimidine and 158 mg of m-methoxyaniline were dissolved in 3 mL of i-PrOH. To the mixture obtained 0.25 mL of 37% HCl were added. The mixture obtained was refluxed at 84° C. for 2.5 hours under a nitrogen atmosphere. A colorless precipitate was formed which was collected by filtration. 6-Chloro-N-(3-methoxyphenyl)pyrimidin-4-amine in the form of a hydrochloride was obtained in the form of a colorless solid.

Yield: 33% of theory.

$^1$H NMR (DMSO-D$_6$, 200 MHz): δ=3.74 (s, 3H), 6.65 (d, J=7.4 Hz, 1H), 6.85 (s, 1H), 7.12-7.37 (m, 3H), 8.49 (s, 1H), 10.02 (s, 1H).

$^{13}$C NMR (DMSO-D$_6$, 50 MHz): δ=55.1 (q), 105.1 (d), 106.3 (d), 108.5 (d), 112.5 (d), 129.4 (d), 140.2 (s), 157.7 (s), 158.5 (s), 159.7 (s), 161.3 (s).

22b. 2-(6-(3-Methoxyphenylamino)pyrimidin-4-ylamino)ethan-1-ol

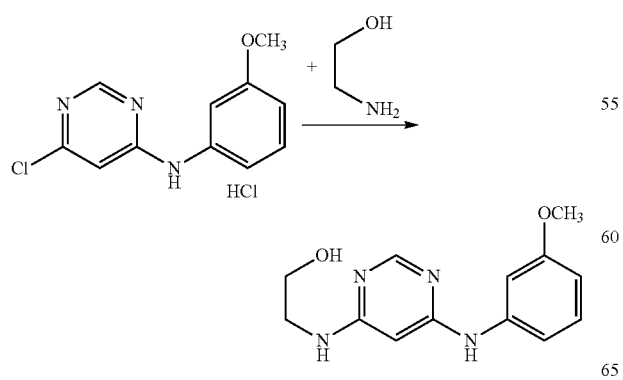

100 mg of 6-chloro-N-(3-methoxyphenyl)pyrimidin-4-amine, 27 mg of ethanolamine and 119 mg of DIPEA were dissolved in 2 mL of n-BuOH and the mixture obtained was charged into a microwave vial and the vial obtained was heated to 200° C. for 45 minutes under microwave irradiation. Progress of the reaction was monitored by TLC. Upon termination of the reaction n-BuOH was evaporated off and to the evaporation residue obtained 5 mL of water were added. The mixture obtained was extracted with EtOAc, the phases were separated and the organic phase obtained was dried and subjected to evaporation. 2-(6-(3-Methoxyphenylamino)pyrimidin-4-ylamino)ethan-1-ol was obtained in the form of a yellow oil.

Yield: 84% of theory.

$^1$H NMR (DMSO-D$_6$, 200 MHz): δ=3.21-3.27 (m, 2H), 3.48 (s, 2H), 3.72 (s, 3H), 4.73 (t, J=5.3 Hz, 1H), 5.82 (s, 1H), 6.49 (d, J=8.2 Hz, 1H), 6.87 (s, 1H), 7.01-7.21 (m, 3H), 8.07 (s, 1H), 8.87 (s, 1H).

$^{13}$C NMR (DMSO-D$_6$, 50 MHz): δ=42.9 (t), 54.8 (q), 59.7 (t), 81.8 (d), 105.1 (d), 106.5 (d), 111.5 (d), 129.4 (d), 141.9 (s), 157.3 (d), 159.3 (s), 159.7 (s), 162.9 (s).

HR-MS: Predicted [MH]$^+$=261.1346; Measured [MH]$^+$=261.1349.

EXAMPLE 23

2-(6-(Phenylamino)pyrimidin-4-ylamino)ethan-1-ol

23a. 6-Chloro-N-phenylpyrimidin-4-amine hydrochloride

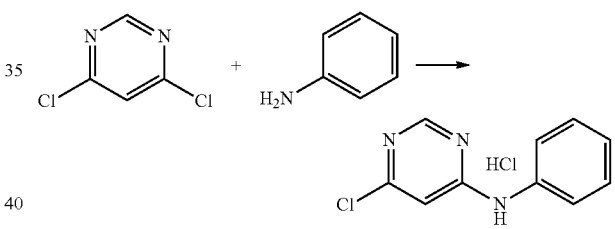

250 mg of 4,6-dichloropyrimidine and 120 mg of aniline were dissolved in 2.5 mL of i-PrOH and 0.25 mL of 37% HCl was added. The mixture obtained was refluxed (84° C.) for 2.5 hours under nitrogen atmosphere. A colorless precipitate was formed which was collected by filtration. 6-Chloro-N-phenylpyrimidin-4-amine hydrochloride in the form of colorless crystals was obtained.

Yield: 40%. of theory. M.p.: 152-155° C.

$^1$H NMR (DMSO-D$_6$, 200 MHz): δ=6.41 (d, J=2.5 Hz, 1H), 6.56 (t, J=7.3 Hz, 1H), 6.74 (m, 3H), 7.16 (d, J=8.0 Hz, 2H), 7.96 (s, 1H), 9.62-9.87 (bs, 1H).

$^{13}$C NMR (DMSO-D$_6$, 50 MHz): δ=105.3 (d), 120.3 (d), 122.9 (d), 129.0 (d), 130.0 (s), 139.0 (s), 158.1 (d), 161.3 (s).

23b. 2-(6-(phenylamino)pyrimidin-4-ylamino)ethan-1-ol

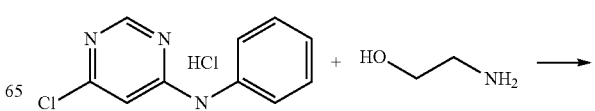

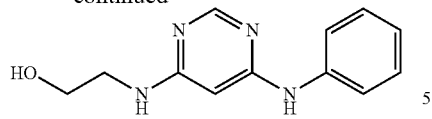

50 mg of 6-chloro-N-phenylpyrimidin-4-amine hydrochloride, 14 mg of ethanolamine and 69 mg of DIPEA were dissolved in 1 mL of n-BuOH and charged into a microwave vial and the vial obtained was heated to 200° C. for 45 minutes under microwave irradiation. The reaction was monitored by TLC. The crude product was obtained by evaporating n-BuOH. Purification was carried out by column chromatography using EtOAc: MeOH 10:1. 2-(6-(Phenylamino)pyrimidin-4-ylamino)ethan-1-ol in the form of a colorless solid was obtained.

Yield: 97%. of theory.

$^1$H NMR (CD$_3$OD, 200 MHz): δ=3.32-3.41 (m, 2H), 3.68 (t, J=5.6 Hz, 2H), 5.84 (s, 1H), 6.99-7.14 (m, 1H), 7.24-7.40 (m, 4H), 8.03 (s, 1H).

$^{13}$C NMR (CD$_3$OD, 50 MHz): δ=28.8 (t), 61.7 (t), 84.1 (d), 122.8 (d), 124.6 (d), 130.1 (d), 140.9 (s), 159.3 (d), 161.9 (s), 164.3 (s).

EXAMPLE 24

2-(6-(4-Chlorophenylamino)pyrimidin-4-ylamino)ethan-1-ol 24a. 6-chloro-N-(4-chlorophenyl)pyrimidin-4-amine hydrochloride

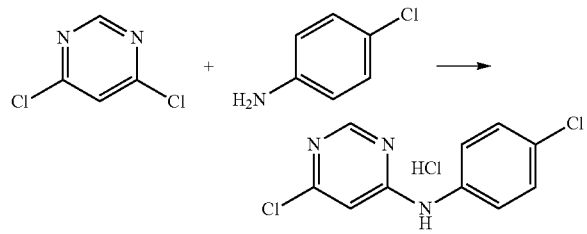

250 mg of 4,6-dichloropyrimidine and 165 mg of p-chloroaniline were dissolved in 2.5 mL of i-PrOH and 0.25 mL of 37% HCl were added. The mixture obtained was refluxed (84° C.) for 2.5 hours under nitrogen atmosphere. A colorless precipitate was formed which was collected by filtration. 6-Chloro-N-(4-chlorophenyl)pyrimidin-4-amine hydrochloride in the form of colorless crystals was obtained.

Yield: 75% of theory. M.p.: 203-212° C.

$^1$H NMR (DMSO-D$_6$, 200 MHz): δ=6.98 (s, 1H), 7.37 (d, J=8.61 Hz, 2H), 7.73 (d, J=8.61 Hz, 2H), 8.48 (s, 1H), 10.51 (s, 1H), 12.19 (s, 1H).

$^{13}$C NMR (DMSO-D$_6$, 50 MHz): δ=105.5 (d), 121.5 (d), 126.5 (s), 128.6 (d), 138.1 (s), 157.6 (s), 158.2 (d), 160.0 (s).

24b. 2-(6-(4-chlorophenylamino)pyrimidin-4-ylamino)ethan-1-ol

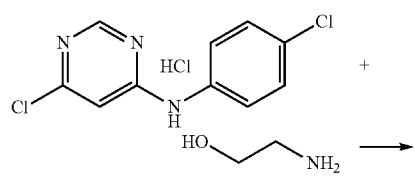

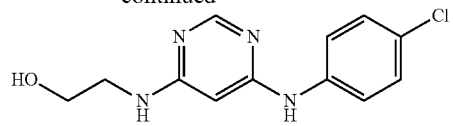

75 mg of 6-chloro-N-(4-chlorophenyl)pyrimidin-4-amine hydrochloride, 18 mg of ethanolamine and 87 mg of DIPEA were dissolved in n-BuOH (1 mL) and the mixture obtained was charged into a microwave vial and the vial obtained was heated to 200° C. for 45 minutes under microwave irradiation. The reaction was monitored by TLC. The crude product was obtained by evaporating n-BuOH. Purification was carried out by column chromatography using EtOAc: MeOH 10:1. 2-(6-(4-Chlorophenylamino)pyrimidin-4-ylamino)ethan-1-ol in the form of a colorless solid was obtained.

Yield: 67% of theory. M.p: 183° C.

$^1$H NMR (CD$_3$OD, 200 MHz): δ=3.37 (t, J=5.7 Hz, 2H), 3.65 (t, J=5.7 Hz, 2H), 5.81 (s, 1H), 7.26 (d, J=8.9 Hz, 2H), 7.40 (d, J=8.9 Hz, 2H), 8.05 (s, 1H).

$^{13}$C NMR (CD$_3$OD, 50 MHz): δ=44.5 (t), 61.8 (q), 84.8 (d), 123.5 (d), 128.7 (s), 129.9 (d), 140.2 (s), 158.6 (d), 161.8 (s), 164.3 (s).

EXAMPLE 25

2-(6-(3-Chlorophenylamino)pyrimidin-4-ylamino)ethan-1-ol 25a. 6-Chloro-N-(3-chlorophenyl)pyrimidin-4-amine hydrochloride

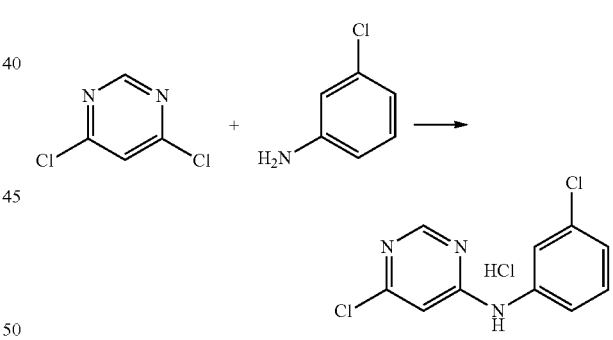

250 mg of 4,6-dichloropyrimidine and 165 mg of m-chloroaniline were dissolved in 2.5 mL of i-PrOH and 0.25 mL of 37% HCl were added. The mixture obtained was refluxed (84° C.) for 2.5 hours under nitrogen atmosphere. A colorless precipitate was formed which was collected by filtration. 6-Chloro-N-(3-chlorophenyl)pyrimidin-4-amine hydrochloride in the form of colorless crystals was obtained.

Yield: 61% of theory M.p.: 166° C.

$^1$H NMR (DMSO-D$_6$, 200 MHz): δ=6.99 (s, 1H), 7.08 (d, J=7.8 Hz, 1H), 7.34 (t, J=8.1 Hz, 1H), 7.57 (d, J=8.2 Hz, 1H), 7.97 (s, 1H), 8.53 (s, 1H), 10.54 (s, 1H), 10.82 (s, 1H).

$^{13}$C NMR (DMSO-D$_6$, 50 MHz): δ=105.8 (d), 118.3 (d), 119.2 (d), 122.4 (d), 130.0 (s), 140.7 (s), 157.7 (s), 158.3 (d), 160.9 (s).

25b. 2-(6-(3-chlorophenylamino)pyrimidin-4-ylamino)ethan-1-ol

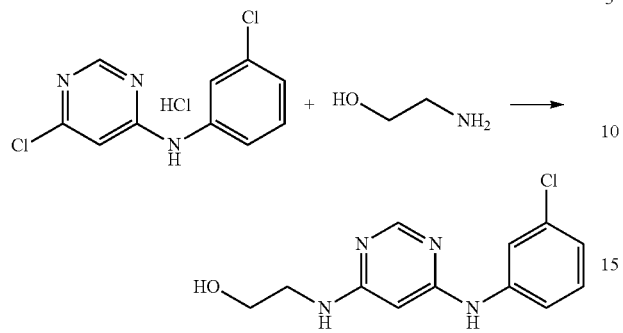

75 mg of 6-chloro-N-(3-chlorophenyl)pyrimidin-4-amine hydrochloride, 24 mg of ethanolamine and 87 mg of DIPEA were dissolved in 1 mL of n-BuOH and charged into a microwave vial and the vial obtained was heated to 200° C. for 45 minutes under microwave irradiation. The reaction was monitored by TLC. The crude product was obtained by evaporating n-BuOH. Purification was carried out by column chromatography using EtOAc: MeOH 10:1. 2-(6-(3-Chlorophenylamino)pyrimidin-4-ylamino)ethan-1-ol in the form of a colorless solid was obtained.

Yield: 68% of theory.
$^1$H NMR (CD$_3$OD, 200 MHz): δ=3.38 (t, J=5.5 Hz, 2H), 3.69 (t, J=5.7 Hz, 2H), 5.84 (s, 1H), 6.98 (td, J$_1$=7.2 Hz, J$_2$=4.9 Hz, 1H), 7.17-7.34 (m, 2H), 7.55-7.61 (m, 1H), 8.09 (s, 1H).
$^{13}$C NMR (CD$_3$OD, 50 MHz): δ=43.0 (t), 60.2 (q), 83.8 (d), 116.1 (d), 119.8 (d), 121.8 (d), 129.6 (d), 133.9 (s), 141.4 (s), 159.0 (d), 160.1 (s), 162.9 (s).

EXAMPLE 26

N$^4$-(3-Chlorophenyl)-N$^6$-cyclohexylpyrimidine-4,6-diamine

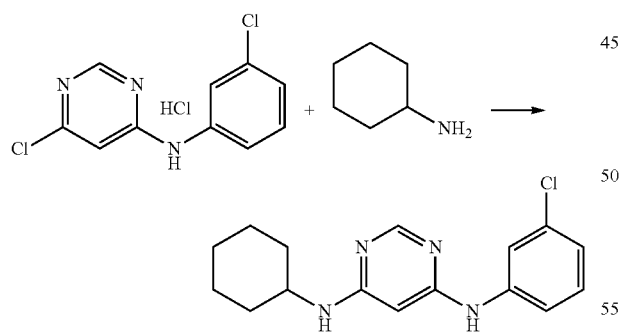

71 mg of 6-chloro-N-(3-chlorophenyl)pyrimidin-4-amine hydrochloride, 29 mg of cyclohexylamine and 84 mg of DIPEA were dissolved in 1 mL of n-BuOH and charged into a microwave vial and the vial obtained was heated to 200° C. for 60 minutes under microwave irradiation. The reaction was monitored by TLC. The crude product was obtained by evaporating n-BuOH. Purification was carried out by column chromatography using PE:EtOAc 1:1. N$^4$-(3-Chlorophenyl)-N$^6$-cyclohexylpyrimidine-4,6-diamine in the form of a colorless solid was obtained.

Yield: 71% of theory.
$^1$H NMR (CDCl$_3$, 200 MHz): δ=1.10-2.12 (m, 1o H), 3.33-3.60 (bs, 1H), 4.97-5.20 (bs, 1H), 5.77 (s, 1H), 7.03-7.22 (m, 2H), 7.28-7.43 (m, 2H), 7.63-7.86 (bs, 1H), 8.21 (s, 1H).
$^{13}$C NMR (CDCl$_3$, 50 MHz): δ=24.7 (t), 25.3 (t), 32.5 (t), 48.7 (d), 84.7 (d), 117.1 (d), 118.1 (d), 120.2 (d), 130.1 (d), 132.9 (s), 142.7 (s), 157.6 (d), 159.5 (s), 161.9 (s).

EXAMPLE 27

N$^4$-(3-Chlorophenyl)-N$^6$-(2-methoxyethyl)pyrimidine-4,6-diamine

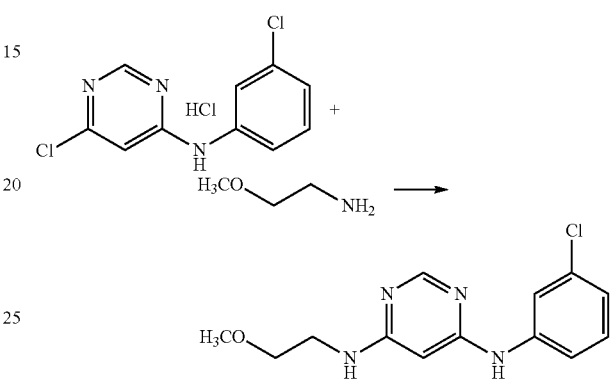

75 mg of 6-chloro-N-(3-chlorophenyl)pyrimidin-4-amine hydrochloride, 30 mg of 2-methoxyethanamine and 88 mg of DIPEA were dissolved in 1 mL of n-BuOH and charged into a microwave vial and the vial obtained was heated to 200° C. for 60 minutes under microwave irradiation. The reaction was monitored by TLC. The crude product was obtained by evaporating n-BuOH. Purification was carried out by column chromatography using EtOAc. N$^4$-(3-Chlorophenyl)-N$^6$-(2-methoxyethyl)pyrimidine-4,6-diamine in the form of a colorless solid was obtained.

Yield: 70% of theory.
$^1$H NMR (CDCl$_3$, 200 MHz): δ=3.37 (s, 3H), 3.39-3.39 (m, 2H), 3.51-3.59 (m, 2H), 5.37-5.53 (bs, 1H), 5.79 (s, 1H), 7.02-7.18 (m, 2H), 7.21-7.27 (m, 1H), 7.29-7.36 (m, 1H), 7.93 (s, 1H), 8.20 (s, 1H).
$^{13}$C NMR (CDCl$_3$, 50 MHz): δ=41.0 (t), 58.8 (q), 70.9 (t), 119.8 (d), 121.7 (d), 123.9 (d), 130.3 (d), 134.9 (s), 140.6 (s), 160.5 (s), 163.3 (s).

EXAMPLE 28

2-(6-(3-Nitrophenylamino)pyrimidin-4-ylamino)ethan-1-ol 28a. 6-Chloro-N-(3-nitrophenyl)pyrimidin-4-amine hydrochloride

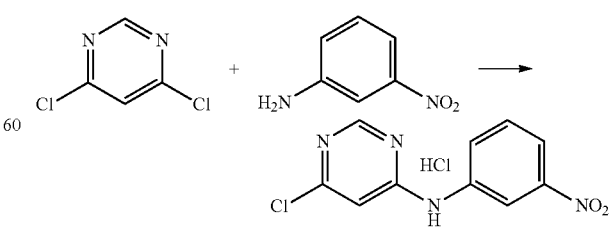

250 mg of 4,6-Dichloropyrimidine and 178 mg of m-nitroaniline were dissolved in 2.5 mL of i-PrOH and 0.25 mL of 37% HCl were added. The mixture obtained was refluxed (84° C.) for 4 hours under nitrogen atmosphere. A colorless precipitate was formed which was collected by filtration. 6-Chloro-N-(3-nitrophenyl)pyrimidin-4-amine hydrochloride in the form of bright yellow crystals was obtained.

Yield: 36% of theory.

$^1$H NMR (DMSO-D$_6$, 200 MHz): δ=7.01 (s, 1H), 7.62 (t, J=8.1 Hz, 1H), 7.89 (dd, J$_1$=8.0 Hz, J$_2$=1.8 Hz, 1H), 8.04 (d, J=8.9 Hz, 1H), 8.60 (s, 1H), 8.78 (s, 1H), 10.74 (bs, 2H).

$^{13}$C NMR (DMSO-D$_6$, 50 MHz): δ=106.2, 113.7, 117.1 125.7, 130.1, 140.5, 147.9, 158.0, 150.4, 160.9.

28b. 2-(6-(3-Nitrophenylamino)pyrimidin-4-ylamino)ethan-1-ol

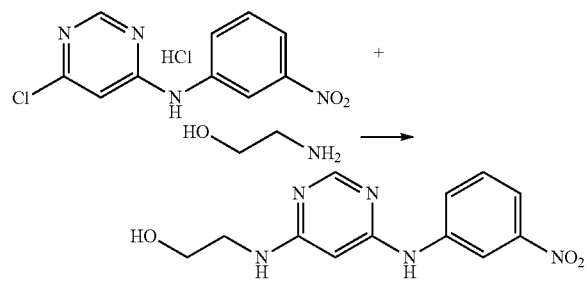

73 mg of 6-chloro-N-(3-nitrophenyl)pyrimidin-4-amine hydrochloride, 23 mg 2-ethanolamine and 81 mg of DIPEA were dissolved in 1 mL of n-BuOH and charged into a microwave vial and the vial obtained was heated to 200° C. for 60 minutes under microwave irradiation. The reaction was monitored by TLC. The crude product was obtained by evaporating n-BuOH. Purification was carried out by column chromatography using EtOAc: MeOH=10:1. 2-(6-(3-Nitrophenylamino)pyrimidin-4-ylamino)ethan-1-ol in the form of a colorless solid was obtained.

Yield: 57% of theory.

$^1$H NMR (CD$_3$OD, 200 MHz): δ=3.40 (t, J=5.7 Hz, 2H), 3.70 (t, J=5.7 Hz, 2H), 5.87 (s, 1H), 7.48 (t, J=8.1 Hz, 1H), 7.82 (dd, J1=8.2 Hz, J2=2.2 Hz, 2H), 8.16 (s, 1H), 8.56 (t, J=2.1 Hz, 1H).

$^{13}$C NMR (CD$_3$OD, 50 MHz): δ=44.5 (d), 61.7 (t), 86.1 (d), 115.1 (d), 117.2 (d), 126.4 (d), 130.7 (d), 143.3 (s), 150.1 (s), 158.1 (6), 161.6 (s), 164.5 (s).

EXAMPLE 29

N$^4$-Cyclohexyl-N$^6$-(3-nitrophenyl)pyrimidine-4,6-diamine

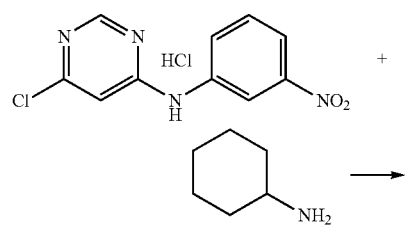

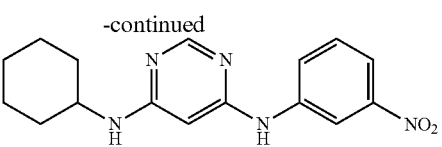

60 mg of 6-chloro-N-(3-nitrophenyl)pyrimidin-4-amine hydrochloride, 32 mg cyclohexylamine and 69 mg of DIPEA were dissolved in 1 mL of n-BuOH and charged into a microwave vial and the vial obtained heated to 200° C. for 60 minutes under microwave irradiation. The reaction was monitored by TLC. The crude product was precipitated from n-BuOH. Purification was carried out by filtering and washing with cold n-BuOH. Pure N$^4$-cyclohexyl-N$^6$-(3-nitrophenyl)pyrimidine-4,6-diamine in the form of a colorless solid was obtained.

Yield: 94% of theory.

$^1$H NMR (DMSO-D$_6$, 200 MHz): δ=0.99-1.94 (m, 10H), 3.56 (s, 1H), 5.79 (s, 1H), 6.93 (d, J=7.6 Hz, 1H), 7.50 (t, J=8.1 Hz, 1H), 7.72 (dd, J$_1$=8.0 Hz, J$_2$=1.9 Hz, 1H), 7.91 (d, J=7.4 Hz, 1H), 8.18 (s, 1H), 8.70 (s, 1H), 9.43 (s, 1H).

$^{13}$C NMR (DMSO-D$_6$, 50 MHz): δ=24.7 (t), 25.3 (t), 32.5 (t), 48.7 (d), 85.2 (d), 112.5 (d), 115.0 (d), 124.6 (d), 129.8 (d), 142.5 (s), 148.0 (s), 157.9 (d), 159.4 (s), 161.9 (s).

EXAMPLE 30

2-(6-(4-Nitrophenylamino)pyrimidin-4-ylamino)ethan-1-ol

30a. 6-Chloro-N-(4-nitrophenyl)pyrimidin-4-amine hydrochloride

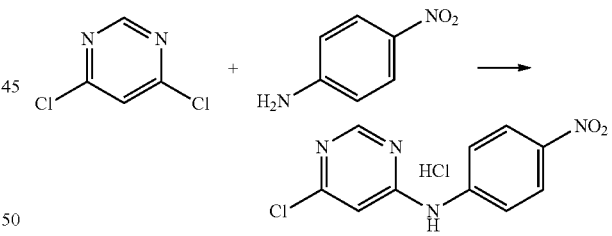

250 mg of 4,6-dichloropyrimidine and 178 mg of p-nitroaniline were dissolved in 2.5 mL of i-PrOH and 0.25 mL of 37% HCl were added. The mixture obtained was refluxed (84° C.) for 4 hours under a nitrogen atmosphere. A precipitate was formed which was collected by filtratio. 6-Chloro-N-(4-nitrophenyl)pyrimidin-4-amine hydrochloride in the form of bright yellow crystals was obtained.

Yield: 49%. of theory.

$^1$H NMR (DMSO-D$_6$, 200 MHz): b=6.99 (s, 1H), 7.95 (d, J=9.19 Hz, 2H), 8.26 (d, J=9.19 Hz, 2H), 8.66 (s, 1H), 10.55 (s, 1H).

$^{13}$C NMR (DMSO-D$_6$, 50 MHz): δ=106.9 (d), 119.0 (d), 125.0 (d), 141.5 (s), 145.6 (s), 158.4 (d), 160.6 (s).

30b. 2-(6-(4-Nitrophenylamino)pyrimidin-4-ylamino)ethan-1-ol

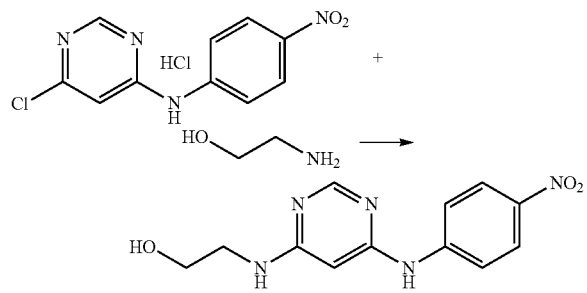

74 mg of chloro-N-(4-nitrophenyl)pyrimidin-4-amine hydrochloride, 23 mg of 2-ethanolamine and 84 mg of DIPEA were dissolved in 1 mL of n-BuOH and charged into a microwave vial and the vial obtained was heated to 200° C. for 60 minutes under microwave irradiation. The reaction was monitored by TLC. The crude product was obtained by evaporating n-BuOH. Purification was carried out by column chromatography using EtOAc: MeOH=10:1. Pure 2-(6-(4-nitrophenylamino)pyrimidin-4-ylamino)ethan-1-ol in the form of a colorless solid was obtained.

Yield: 94% of theory.

$^1$H NMR (DMSO-D$_6$, 200 MHz): δ=1.03-1.96 (m, 10H), 3.49-3.51 (bs, 1H), 5.90 (s, 1H), 7.05 (d, J=7.4 Hz, 1H), 7.85 (d, J=9.2 Hz, 2H), 8.13 (s, 1H), 8.19 (d, J=6.8 Hz, 2H), 9.74 (s, 1H).

$^{13}$C NMR (DMSO-D$_6$, 50 MHz): δ=24.6 (t), 25.4 (t), 32.6 (t), 49.1 (d), 117.5 (d), 125.3 (d), 139.8 (s), 148.0 (s), 157.5 (d), 158.9 (s), 162.2 (s).

EXAMPLE 31

3-(6-(3-Chlorophenylamino)pyrimidin-4-ylamino)propan-1-ol

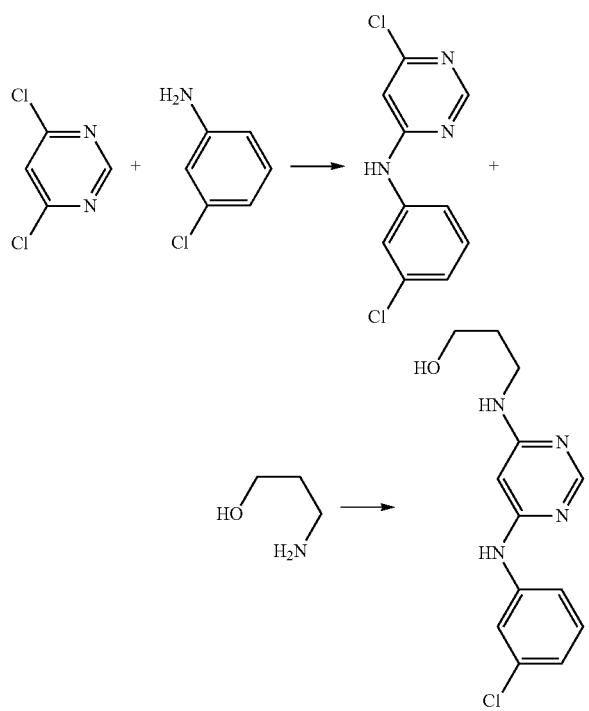

100 mg of 4,6-dichloropyrimidine, 94 mg of m-chloroaniline and 103 mg of DIPEA were dissolved in 1 mL of n-BuOH and the mixture obtained was charged into a microwave vial and the vial obtained was kept overnight in a heating block at 120° C. The reaction was monitored by TLC and was completed within the next day. The mixture obtained was cooled to r.t., 76 mg of propanolamine and 139 mg of DIPEA were added and the mixture obtained was heated under microwave irradiation for an hour at 200° C. The reaction was finished and crude product was obtained by evaporating n-BuOH. Purification was carried out by column chromatography using EtOAc: MeOH 20:1.

3-(6-(3-Chlorophenylamino)pyrimidin-4-ylamino)propan-1-ol in the form of a colorless solid was obtained.

Yield: 75% of theory.

$^1$H NMR (CD$_3$OD, 200 MHz): δ=1.70-1.88 (m, 2H), 3.32-3.40 (m, 2H), 3.65 (t, J=6.2 Hz, 2H), 5.80 (s, 1H), 6.91-7.04 (m, 1H), 7.15-7.35 (m, 2H), 7.59 (s, 1H), 8.08 (s, 1H).

$^{13}$C NMR (CD$_3$OD, 50 MHz): δ=33.1 (t), 39.1 (t), 60.4 (t), 84.9 (d), 119.7 (d), 121.3 (d), 123.3 (d), 131.1 (d), 135.5 (s), 143.0 (s), 158.6 (d), 161.7 (s), 164.4 (s).

EXAMPLE 32

2-(6-(3-Fluorophenylamino)pyrimidin-4-ylamino)ethan-1-ol

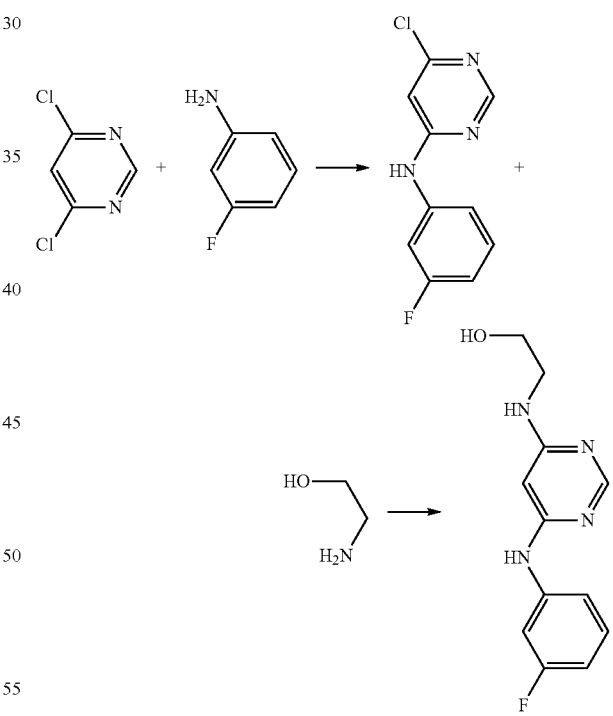

100 mg of 2,6-dichloropyrimidine, 82 mg of m-fluoroaniline and 103 mg of DIPEA in 1 mL of n-BuOH were charged into a microwave vial and the vial obtained was kept in a heating block at 120° C. for 4 hours. The reaction was monitored by TLC and was completed in 4 h. The mixture obtained was cooled to r.t., 61 mg ethanolamine and 139 mg of DIPEA were added and the mixture obtained was heated under microwave irradiation for an hour at 200° C. The reaction was finished and crude product was obtained by evaporating n-BuOH. Purification was carried out by column chromatography using EtOAc: MeOH 20:1. 2-(6-(3-Fluorophenylamino)pyrimidin-4-ylamino)ethan-1-ol in the form of a colorless solid was obtained.

Yield: 72% of theory.

$^1$H NMR (CD$_3$OD, 200 MHz): δ=3.38 (t, J=5.6 Hz, 2H), 3.69 (t, J=5.6 Hz, 2H), 5.86 (s, 1H), 6.62-6.79 (m, 1H), 7.06-7.18 (m, 1H), 7.19-7.30 (m, 1H), 7.31-7.43 (m, 1H), 8.09 (s, 1H).

$^{13}$C NMR (CD$_3$OD, 50 MHz): δ=44.6 (t), 61.7 (t), 85.3 (s), 108.39 (dd), 109.8 (dd), 131.1 (dd), 143.4 (dd), 158.6 (d), 161.9 (dd), 165.7 (d).

EXAMPLE 33

2-(6-(3-Bromophenylamino)pyrimidin-4-ylamino)ethan-1-ol

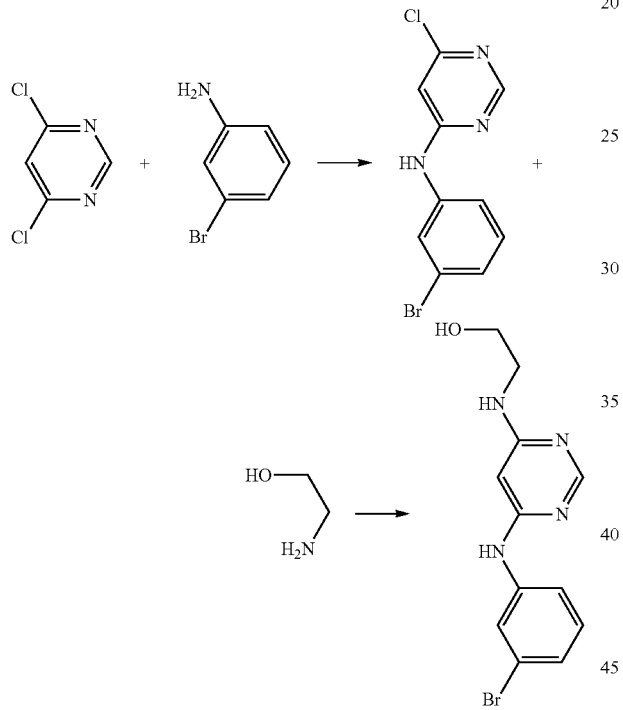

100 mg of 4,6-dichloropyrimidine, 127 mg of m-bromoaniline and 103 mg of DIPEA were dissolved in 1 mL of n-BuOH and the mixture obtained was charged into a microwave vial and the vioal obtained was kept in a heating block at 120° C. for 6 hours. The reaction was monitored by TLC and was completed within 6 hours. The mixture obtained was cooled to r.t., 61 mg of ethanolamine and 139 mg of DIPEA were added and the mixture obtained was heated under microwave irradiation for an hour at 200° C. The reaction was finished and crude product was obtained by evaporating n-BuOH. Purification was carried out by column chromatography using EtOAc: MeOH 20:1. 2-(6-(3-Bromophenylamino)pyrimidin-4-ylamino)ethan-1-ol in the form of a colorless solid was obtained.

Yield: 60% of theory.

$^1$H NMR (CD$_3$OD, 200 MHz): δ=3.39 (t, J=5.6 Hz, 2H), 3.69 (t, J=5.6 Hz, 2H), 5.85 (s, 1H), 6.62-6.79 (m, 1H), 7.09-7.26 (m, 1H), 7.31-7.43 (m, 1H), 7.69-7.78 (m, 1H), 8.09 (s, 1H).

$^{13}$C NMR (CD$_3$OD, 50 MHz): δ=44.6 (t), 61.8 (t), 85.4 (s), 120.2 (d), 123.4 (s), 124.3 (d), 126.4 (d), 131.4 (d), 143.1 (s), 158.6 (d), 161.6 (s), 164.4 (s).

EXAMPLE 34

Ethyl 4-(6-(2-hydroxyethylamino)pyrimidin-4-ylamino)benzoate

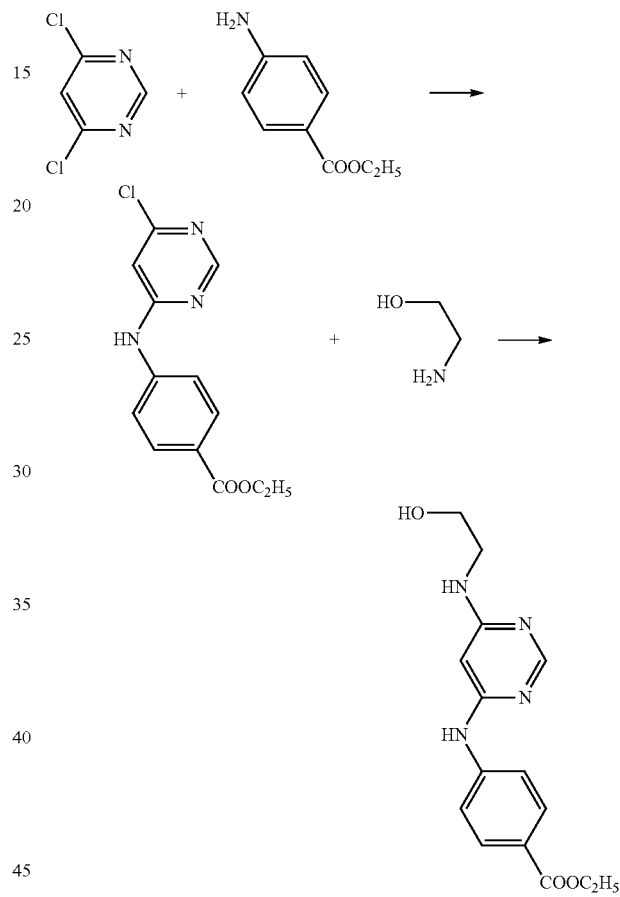

100 mg of 4,6-dichloropyrimidine, 122 mg of ethyl-4-aminobenzoate and 103 mg of DIPEA were dissolved in 1 mL of n-BuOH and the mixture obtained was charged into a microwave vial and the vial obtained was kept in a heating block at 120° C. for 6 hours. The reaction was monitored by TLC and was completed within 6 hours. The mixture obtained was cooled to r.t., 61 mg of ethanolamine and 139 mg of DIPEA were added and the mixture obtained was heated under microwave irradiation for an hour at 200° C. The reaction was finished and crude product was obtained by evaporating n-BuOH. Purification was carried out by column chromatography using EtOAc: MeOH 20:1. Ethyl 4-(6-(2-hydroxyethylamino)pyrimidin-4-ylamino)benzoate in the form of a colorless solid was obtained.

Yield: 67% of theory.

$^1$H NMR (CD$_3$OD, 200 MHz): δ=1.38 (t, J=7.1 Hz, 3H), 3.40 (t, J=5.7 Hz, 2H), 3.70 (t, J=5.7 Hz, 2H), 4.33 (q, J=7.1 Hz, 2H), 5.94 (s, 1H), 7.58 (d, J=8.8 Hz, 2H), 7.93 (d, J=8.8 Hz, 2H), 8.13 (s, 1H).

$^{13}$C NMR (CD$_3$OD, 50 MHz): δ=14.7 (t), 44.6 (d), 61.7 (d), 61.8 (d), 86.5 (d), 115.7 (d), 124.4 (s), 131.6 (d), 146.6 (s), 158.6 (d), 161.3 (d), 164.6 (d), 168.0 (d).

EXAMPLE 35

2-(6-(3-Chloro-4-methoxyphenylamino)pyrimidin-4-ylamino)ethan-1-ol

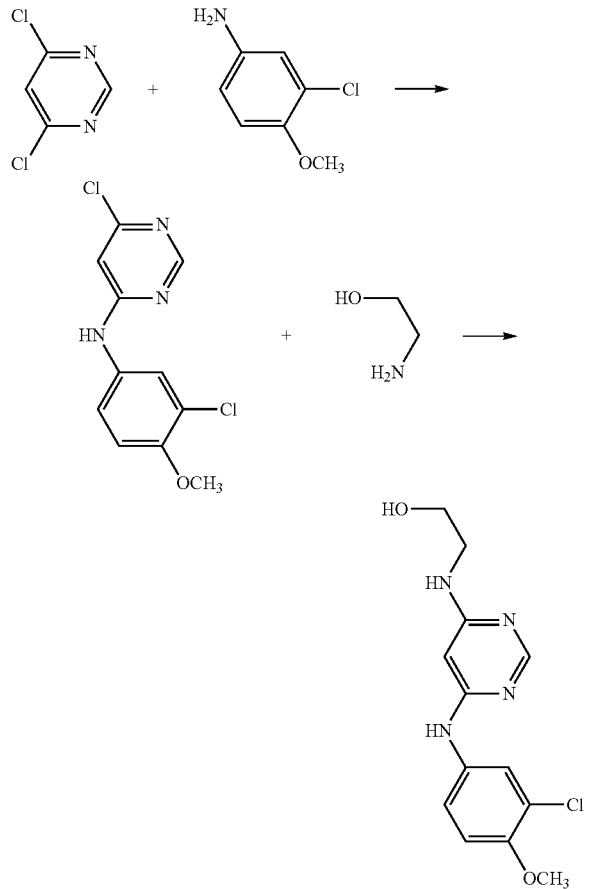

100 mg of 4,6-dichloropyrimidine, 106 mg of 3-chloro-4-methoxyaniline and 103 mg of DIPEA were dissolved in 1 mL n-BuOH and the mixture obtained was charged into a microwave vial and the vial obtained was kept overnight in a heating block at 120° C. The reaction was monitored by TLC and was completed after 12 hours. The mixture obtained was cooled to r.t., 61 mg of ethanolamine and 139 mg of were added and the mixture obtained was heated under microwave irradiation for an hour at 200° C. The reaction was finished and crude product was obtained by evaporating n-BuOH. Purification was carried out by column chromatography using EtOAc:MeOH 20:1. 2-(6-(3-Chloro-4-methoxyphenylamino)pyrimidin-4-ylamino)ethan-1-ol in the form of a colorless solid was obtained.

Yield: 51% of theory.

$^1$H NMR (CD$_3$OD, 200 MHz): δ=3.34-3.41 (m, 2H), 3.67 (t, J=5.7 Hz, 2H), 3.86 (s, 3H), 5.71 (s, 1H), 7.02 (d, J=8.8 Hz, 1H), 7.24 (dd, J$_1$=8.2 Hz, J$_2$=2.5 Hz, 1H), 7.45 (d, J=2.5 Hz, 1H), 8.02 (s, 1H).

$^{13}$C NMR (CD$_3$OD, 50 MHz): δ=44.5 (t), 56.9 (q), 61.8 (t), 83.9 (d), 113.9 (d), 123.9 (d), 123.0 (d), 123.5 (s), 134.6 (s), 153.0 (s), 158.6 (d), 162.3 (s), 164.4 (s).

EXAMPLE 36

N$^4$-(3-Chloro-4-methoxyphenyl)-N$^6$-cyclohexylpyrimidine-4,6-diamine

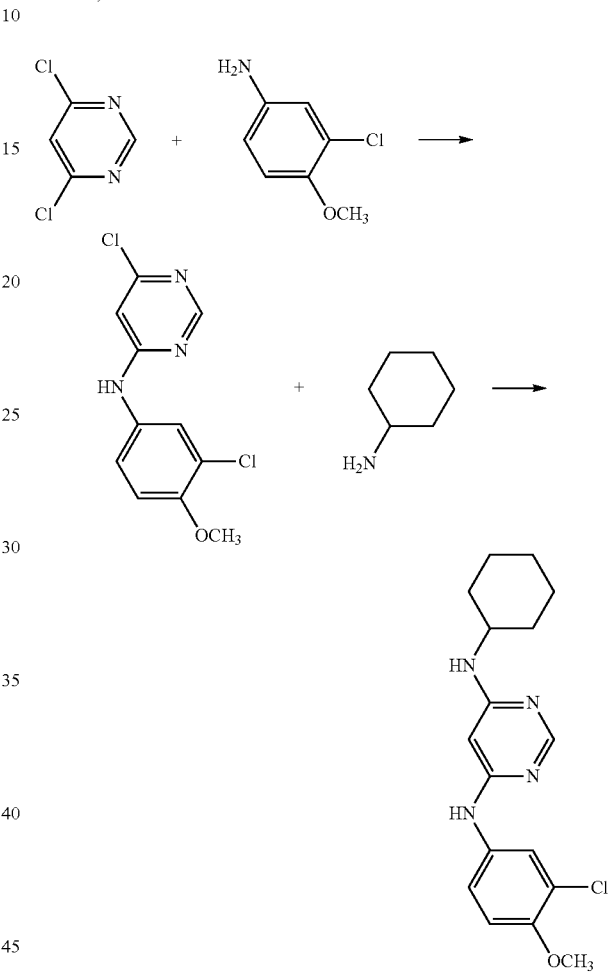

100 mg of 4,6-dichloropyrimidine, 106 mg of 3-chloro-4-methoxyaniline and 103 mg of DIPEA were dissolved in 1 mL n-BuOH and the mixture obtained was charged into a microwave vial and kept overnight in a heating block at 120° C. The reaction was monitored by TLC and was completed after 12 hours. The mixture obtained was cooled to r.t., 100 mg of cyclohexylamine and 139 mg of DIPEA were added and mixture obtained was heated under microwave irradiation for an hour at 200° C. The reaction was finished and pure product was precipitated out from n-BuOH. The precipitate obtained was washed with cold n-BuOH. Pure N$^4$-(3-chloro-4-methoxyphenyl)-N$^6$-cyclohexylpyrimidine-4,6-diamine in the form of a colorless solid was obtained.

Yield: 70% of theory.

$^1$H NMR (DMSO-D$_6$, 200 MHz): δ=1.02-1.95 (m, 10H), 3.48-3.71 (bs, 1H), 3.81 (s, 3H), 5.66 (s, 1 h), 6.74 (d, J=7.6 Hz, 1H), 7.06 (d, J=8.9 Hz, 1H), 7.33 (dd, J$_1$=8.8 Hz, J$_2$=2.5 Hz, 1H), 7.73 (d, J=2.3 Hz, 1H), 8.07 (s, 1H), 8.80 (s, 1H).

$^{13}$C NMR (DMSO-D$_6$, 50 MHz): δ=24.6 (t), 15.3 (t), 32.6 (t), 48.7 (d), 56.2 (q), 83.6 (d), 113.0 (d), 119.4 (d), 120.6 (s), 121.3 (d), 134.7 (s), 149.2 (s), 157.6 (d), 159.9 (s), 161.8 (s).

EXAMPLE 37

N$^4$-Cyclohexyl-N$^6$-(3-methoxyphenyl)pyrimidine-4,6-diamine

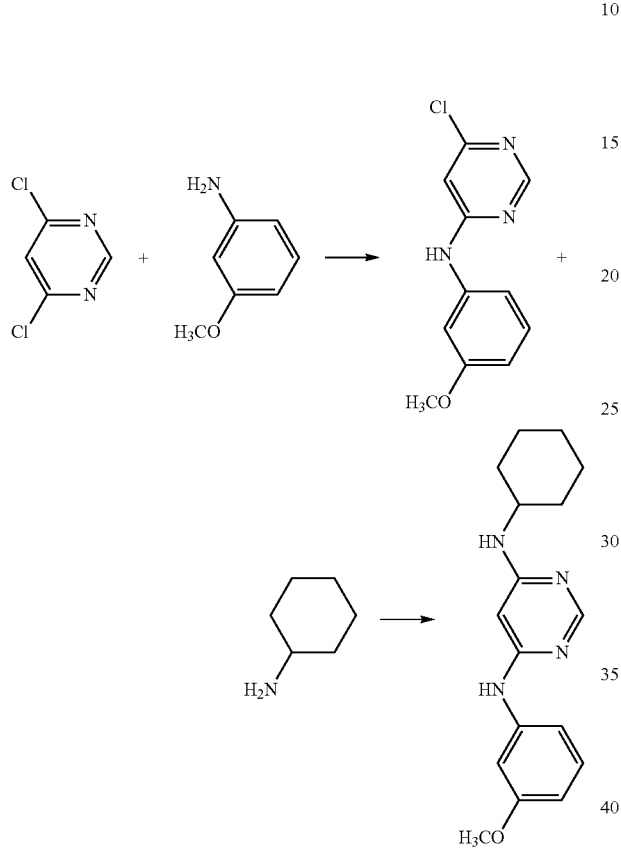

100 mg of 4,6-dichloropyrimidine, 83 mg of 3-methoxyaniline and 103 mg of DIPEA were dissolved in 1 mL of n-BuOH and the mixture obtained was charged into a microwave vial and the vial obtained was kept in a heating block at 120° C. for 6 hours. The reaction was monitored by TLC and was completed after 6 hours. The mixture obtained was cooled to r.t., 100 mg of cyclohexylamine and 139 mg of DIPEA were added and the mixture obtained was heated under microwave irradiation for an hour at 200° C. The reaction was finished and pure product was purified by column chromatography using PE:EtOAc 2:1. Pure N$^4$-Cyclohexyl-N$^6$-(3-methoxyphenyl)pyrimidine-4,6-diamine in the form of a colorless solid was obtained.

Yield: 65% of theory.

$^1$H NMR (CDCl$_3$, 200 MHz): δ=1.00-2.07 (m, 10H), 3.26-3.52 (bs, 1H), 3.71 (s, 3H), 5.12-5.38 (bs, 1H), 5.80 (s, 1H), 6.5-6.71 (m, 1H), 6.78-6.90 (m, 2H), 7.16-7.31 (m, 1H), 8.04-8.21 (m, 2H).

$^{13}$C NMR (CDCl$_3$, 50 MHz): δ=24.7 (t), 25.6 (t), 32.9 (t), 49.8 (q), 55.2 (d), 81.7 (d), 107.6 (d), 107.6 (d), 109.5 (d), 114.3 (d), 130.0 (d), 140.6 (s), 158.3 (d), 160.5 (d), 160.9 (s), 162.3 (s).

EXAMPLE 38

2-(6-((4-Methoxyphenyl)(methyl)amino)pyrimidin-4-ylamino)ethan-1-ol

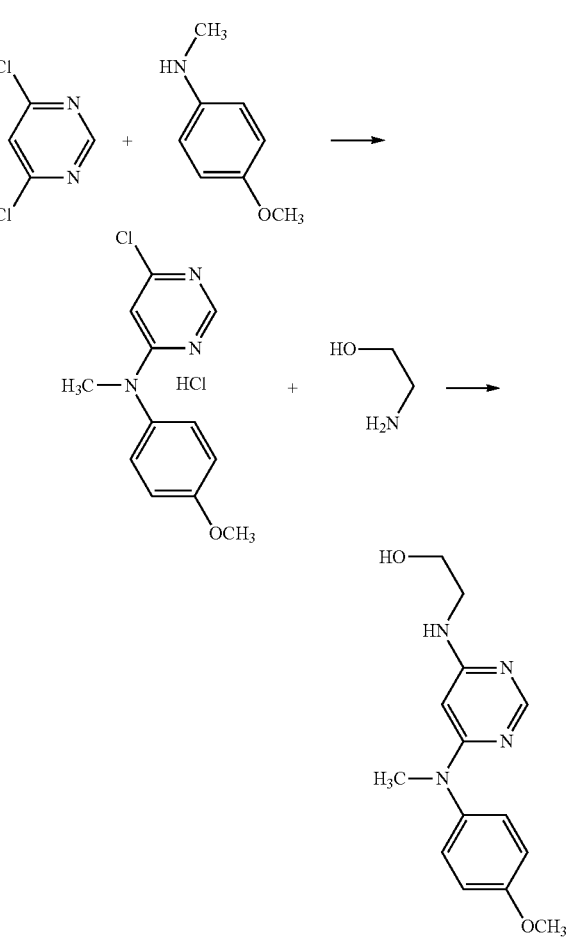

100 mg of 4,6-Dichloropyrimidine, 83 mg of 4-methoxy-N-methylaniline and 0.1 mL of c.HCl were dissolved in 1 mL of i-PrOH and charged into a screw cap vial and kept in a heating block at 90° C. for overnight. The reaction was monitored by TLC and was completed after 12 h. After cooling to r.t., solvent was evaporated and the residue was redissoved in 1 mL of n-BuOH and taken in a microwave vial. 26 mg of Ethanolamine and 106 mg of DIPEA were added and the reaction mixture was heated under microwave irradiation for 45 min at 200° C. The reaction was finished and pure product was purified by column chromatography using EtOAc. Pure 2-(6-((4-methoxyphenyl)(methyl)amino)-pyrimidin-4-ylamino)ethan-1-ol in the form of a colorless solid was obtained.

Yield: 41% of theory.

$^1$H NMR (CDCl$_3$, 200 MHz): δ=3.27 (bs, 2H), 3.38 (s, 3H), 3.68 (t, J=4.0 Hz, 2H), 3.83 (s, 3H), 5.11 (s, 1H), 5.16 (s, 1H), 6.93 (d, J=8.8 Hz, 2H), 7.12 (d, J=8.6 Hz, 2H), 8.16 (s, 1H).

$^{13}$C NMR (CDCl$_3$, 50 MHz): δ=38.2 (t), 44.2 (q), 55.5 (t), 61.9 (q), 82.6 (d), 115.1 (d), 128.4 (d), 137.7 (s), 157.2 (d), 158.2 (s), 162.1 (s), 163.1 (s).

EXAMPLE 39

2-(6-(Cyclohexylamino)pyrimidin-4-ylamino)ethan-1-ol

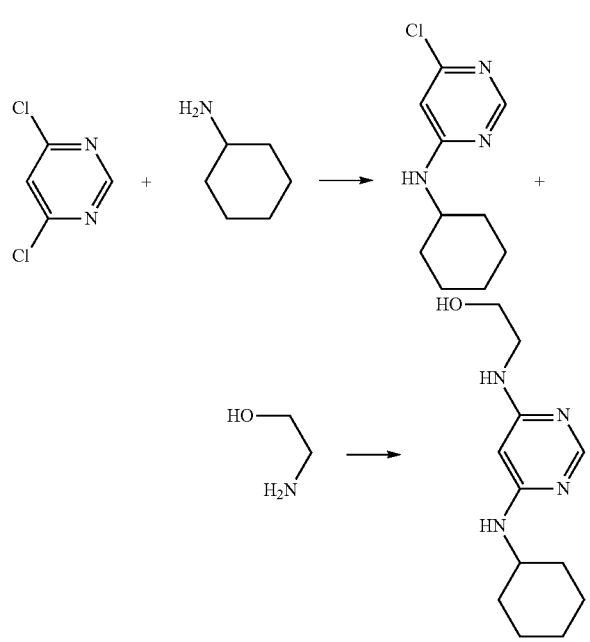

250 mg of 4,6-dichloropyrimidine, 117 mg of cyclohexylamine and 261 mg of DIPEA were dissolved in 1 mL of i-PrOH and the mixture obtained was charged into a screw cap vial and the vial obtained was kept in a heating block at 90° C. for 6 hours. The reaction was monitored by TLC and was completed after 6 hours. The mixture obtained was cooled to r.t., solvent was evaporated and the evaporation residue was redissoved in 1 mL of n-BuOH and taken in a microwave vial. To the mixture in the vial 113 mg of ethanolamine and 206 mg of DIPEA were added and the mixture obtained was heated in a reaction block at 180° C. for 1 hour. The reaction was finished and pure product was purified by column chromatography using EtOAc:MeOH 10:1. Pure 2-(6-(Cyclohexylamino)pyrimidin-4-ylamino)ethan-1-ol in the form of a colorless solid was obtained.

Yield: 63% of theory.

$^1$H NMR (CD$_3$OD, 200 MHz): δ=1.07-2.04 (m, 11H), 3.37-3.38 (m, 2H), 3.42-3.59 (bs, 1H), 3.68 (t, J=5.7 Hz, 2H), 5.45 (s, 1H), 7.88 (s, 1H).

$^{13}$C NMR (CD$_3$OD, 50 MHz): δ=26.1 (t), 26.8 (t), 34.0 (t), 44.6 (t), 50.8 (s), 82.0 (d), 158.2 9d), 162.9 (s), 163.9 (s).

EXAMPLE 40

2-(4-(4-Methoxyphenylamino)pyridin-2-ylamino)ethan-1-ol

40a. (2-Fluoro-N-(4-methoxyphenyl)pyridin-4-amine

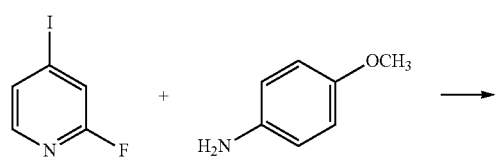

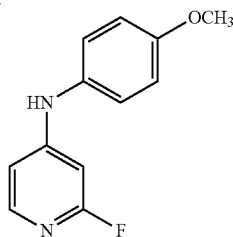

50 mg of 2-fluoro-4-iodopyridine, 33 mg of p-anisidine, 108 mg of K$_2$CO$_3$, 1 mg of Pd(OAc)$_2$ and 6 mg of BINAP were charged into a microwave vial and 2 mL of dry toluene were added and the vial was sealed, evacuated and flushed with Argon. The mixture in the vial was irradiated at 180° C. in a CEM Explorer™ microwave unit for 30 minutes with stirring and the mixture obtained was cooled to r.t. From the mixture obtained solid material was filtered off and washed with 10 mL of CH$_2$Cl$_2$ and solvent from the combined filtrate and washing solvent was evaporated off. The evaporation residue obtained was subjected to flash column chromatography. (2-Fluoro-N-(4-methoxyphenyl)pyridin-4-amine in the form of yellow crystals was obtained.

Yield: 63% of theory. M.p.: 150° C.

$^1$H NMR (CDCl$_3$, 200 MHz): δ=3.83 (s, 3H) 6.20 (d, J=1.7 Hz, 1H) 6.31 (s, 1H) 6.49-6.54 (m, 1H) 6.95 (d, J=8.9 Hz, 2H) 7.14 (d, J=8.8 Hz, 2H) 7.81 (d, J=8.8 Hz, 1H).

$^{13}$C NMR (CDCl$_3$, 50 MHz): δ=55.5 (t) 91.6 (q, J$_{C-F}$=42.4 Hz), 107.5 (q, J$_{C-F}$=2.8 Hz), 114.9 (d), 125.8 (d), 131.4 (s), 147.4 (q, J=18.7 Hz), 156.5 (d, J$_{C-F}$=11.6 Hz), 157.6 (s), 165.5 (d, J$_{C-F}$=232.7 Hz).

Combustion Analysis: Calcd: C, 66.05% H; 5.08% N; 12.84%. Found: C, 65.76%; H. 4.84%; N, 12.62%.

40b. 2-(4-(4-Methoxyphenylamino)pyridin-2-ylamino)ethan-1-ol

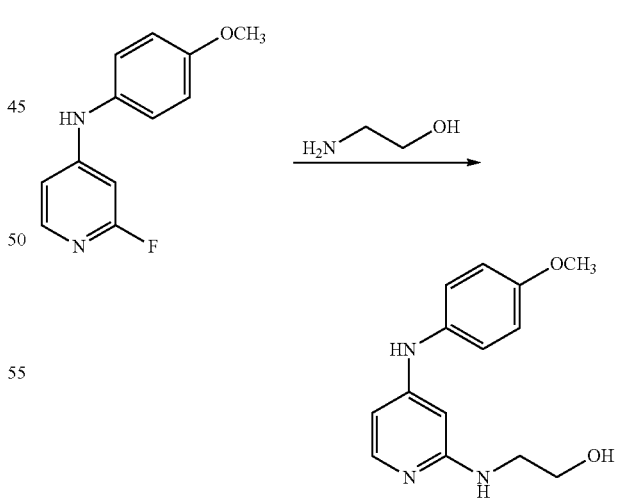

36 mg of (2-fluoro-N-(4-methoxyphenyl)pyridin-4-amine were mixed with 80.6 mg of ethanolamine and the mixture obtained was heated in a screw cap vial under argon to 150° C. for 3 days. The mixture obtained was cooled to r.t. and 5 mL of 2N NaOH were added, the mixture obtained was extracted with EtOAc for three times and from the organic layer obtained solvent was evaporated off. 2-(4-(4-Methoxyphenylamino)pyridin-2-ylamino)ethan-1-ol was obtained in the form of a brown solid.

Yield: 89% of theory. M.p.: 164-165° C.

$^1$H NMR (DMSO-D$_6$, 200 MHz): δ=3.22 (m, 2H), 3.45 (m, 2H), 3.72 (s, 3H), 5.89 (s, 1H), 6.05 (m, 2H), 6.89 (d, J=8.8 Hz, 2H), 7.07 (s, J=8.8 Hz, 2H), 7.59 (s, J=5.7 Hz, 1H), 8.11 (s, 1H).

$^{13}$C NMR (DMSO-D$_6$, 50 MHz): δ=43.8 (t), 55.2 (q), 60.7 (t), 89.3 (d), 114.4 (d), 122.9 (d), 133.9 (s), 147.4 (d), 151.9 (s), 154.9 (s), 159.9 (s).

HR-MS: Predicted [MH]$^+$=260.1394; Measured [MH]$^+$=260.1400.

EXAMPLE 41

2-(4-(4-Phenoxyphenylamino)pyridin-2-ylamino)ethan-1-ol 41a. 2-Fluoro-N-(4-phenoxyphenyl)pyridin-4-amine

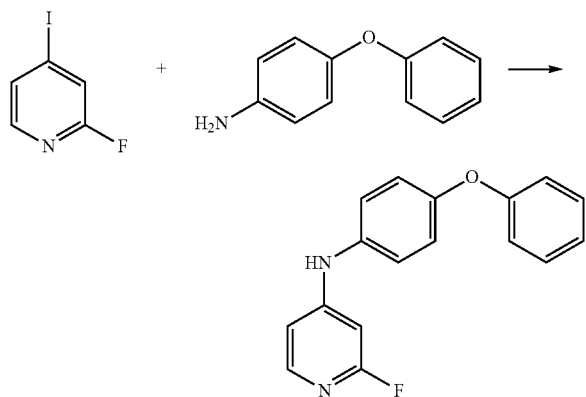

100 mg of 2-fluoro-4-iodopyridine, 100 mg of 4-phenoxyaniline, 218 mg of K$_2$CO$_3$, 2 mg of Pd(OAc)$_2$ and 6 mg of BINAP were charged into a microwave vial and 2 mL of dry toluene were added. The vial was sealed, evacuated and flushed with Argon. The mixture in the vial was irradiated at 180° C. in a CEM Explorer™ microwave unit for 30 minutes with stirring. The mixture obtained was cooled to r.t. From the mixture obtained solid material was filtered off and washed with 10 mL of CH$_2$Cl$_2$ and solvent from the combined filtrate and washing solvent was evaporated off. The evaporation residue obtained was subjected to flash column chromatography.

2-Fluoro-N-(4-phenoxyphenyl)pyridin-4-amine was obtained in the form of brown crystals.

Yield: 75% of theory. M.p.: 149° C.

$^1$H NMR (CDCl$_3$, 200 MHz): δ=6.51 (d, J=1.9 Hz, 1H) 6.61 (s, 1H) 6.81 (d, J=5.8 Hz, 1H) 7.23 (d, J=2.1 Hz, 2H) 7.37 (m, 3H) 7.48 (s, 1H) 7.57 (t, J=7.9 Hz, 3H) 8.80 (d, J=5.8 Hz, 1H)

$^{13}$C NMR (CDCl$_3$, 50 MHz): δ=92.0 (q, J$_{C-F}$=39.5 Hz), 107.8 (q, J$_{C-F}$=3.2 Hz), 118.9 (d), 119.9 (d), 123.5 (d), 125.0 (d), 129.9 (d), 133.9 (s), 147.9 (q, J$_{C-F}$=22.9 Hz), 154.8 (s), 155.8 (d, J$_{C-F}$=11.9 Hz) 157.0 (s), 165.6 (d, J$_{C-F}$=233.0 Hz).

41b. 2-(4-(4-Phenoxyphenylamino)pyridin-2-ylamino)ethan-1-ol

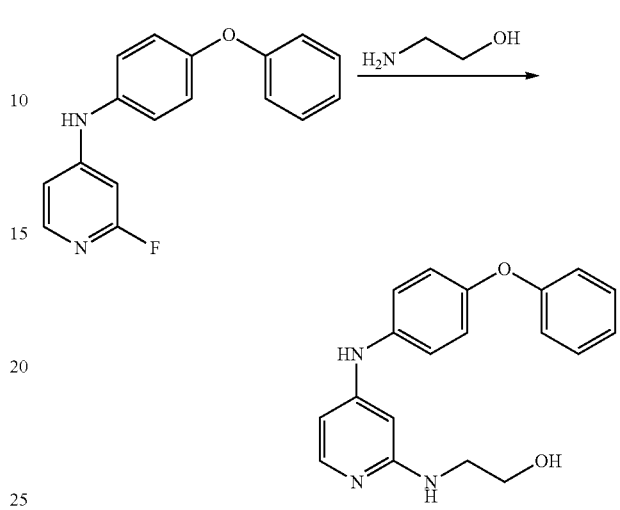

53 mg of 2-fluoro-N-(4-phenoxyphenyl)pyridin-4-amine in 80.6 mg of ethanolamine were heated in a screw cap vial under argon at 150° C. for 3 days. The mixture obtained was cooled to r.t. and 5 mL of 2N NaOH were added. The mixture obtained was extracted with 15 mL of EtOAc for three times. From the mixture obtained organic solvent was evaporated off. 2-(4-(4-Phenoxyphenylamino)pyridin-2-ylamino)ethan-1-ol was obtained.

Yield: 89% of theory.

$^1$H NMR (CD$_3$OD, 200 MHz): δ=3.33-3.37 (m, 2H), 3.68 (t, J=5.5 Hz, 2H), 6.05 (d, J=1.9 Hz, 1H), 6.20 (dd, J$_1$=6.1 Hz, J$_2$=2.2 Hz, 1H), 6.95 (s, 2H), 6.97-7.02 (m, 2H), 7.08 (t, J=7.3 Hz, 1H), 7.14-7.23 (m, 2H), 7.26-7.39 (m, 2H), 7.61 (d, J=6.1 Hz, 1H).

$^{13}$C NMR (CD$_3$OD, 50 MHz): δ=45.5 (t), 62.4 (t), 90.9 (d), 102.8 (d), 119.3 (d), 121.1 (d), 124.1 (d), 124.4 (d), 130.8 (d), 137.8 (s), 147.9 (d), 154.2 (s), 154.5 (s), 159.3 (s), 161.5 (s).

EXAMPLE 42

2-(6-(4-Methoxyphenylamino)pyridin-2-ylamino)ethan-1-ol 42a. 6-Chloro-N-(4-methoxyphenyl)pyridin-2-amine

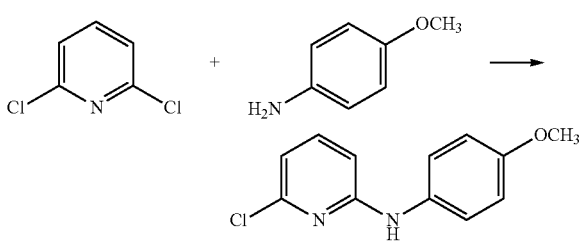

100 mg of 2,6-dichloropyridine, 100 mg of p-anisidine, 329 mg of K$_2$CO$_3$, 3 mg of Pd(OAc)$_2$ and 9 mg of BINAP were charged into a microwave vial and 2.5 mL of dry toluene was added. The vial was sealed, evacuated and flushed with Argon. The mixture in the vial was irradiated at 180° C. in a CEM Explorer™ microwave unit for 30 minutes with stirring. The mixture obtained was cooled to r.t. From the mixture obtained solid material was filtered off and washed with 10 mL of CH$_2$Cl$_2$ and solvent from the combined filtrate and washing solvent was evaporated off. The evaporation residue obtained was subjected to flash column chromatography.

6-Chloro-N-(4-methoxyphenyl)pyridin-2-amine was obtained in the form of a yellow solid.

Yield: 72% of theory. M.p: 74-76° C.

$^1$H NMR (CDCl$_3$, 200 MHz): δ=3.8 (s, 3H), 6.52 (d, J=8.2 Hz, 1H) 6.65 (d, J=7.6 Hz, 1H), 6.74 (s, 1H), 6.89 (d, J=9.4 Hz, 2H), 7.19 (d, J=7.2 Hz, 2H), 7.34 9t, J=7.9 Hz, 1H).

$^{13}$C NMR (CDCl$_3$, 50 MHz): δ=54.6 (q), 103.8 (d), 112.4 (d), 113.8 (d), 123.7 (d), 131.1 (s), 139.1 (d), 148.5 (s), 155.9 (s), 156.4 (s).

Combustion Analysis: Calcd. C, 68.81; H, 4.42; N, 11.95. Found C, 68.60; H, 4.22; N, 8.92.

42b. 2-(6-(4-Methoxyphenylamino)pyridin-2-ylamino)ethan-1-ol

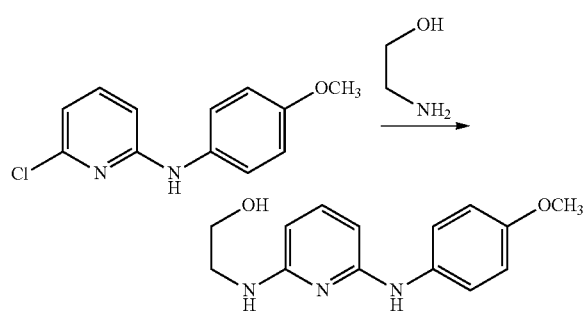

190 mg of 6-chloro-N-(4-methoxyphenyl)pyridin-2-amine were mixed with 397 mg of ethanolamine and the mixture obtained was heated in a screw cap vial under argon at 150° C. for 3 days. The mixture obtained was cooled to r.t. and 5 mL of EtOAc were added, The mixture obtained was extracted with 5 mL of EtOAc for three times, the phases were separated, the organic phase was dried and from the dry mixture obtained solvent was evaporated off. The evaporation residue obtained was subjected to flash column chromatography (EtOAc:PE 3:1). 2-(6-(4-Methoxyphenylamino)pyridin-2-ylamino)ethan-1-ol was obtained in the form of a brown oil.

Yield: 73% of theory.

$^1$H NMR (CDCl$_3$, 200 MHz): δ=3.35 (t, J=4.8 Hz, 2H), 3.80 (s, 3H), 3.84 (t, J=4.6 Hz, 2H), 5.80 (d, J=7.8 Hz, 1H), 5.92 (d, J=9.4 Hz, 2H), 6.89 (d, J=8.9 Hz, 2H), 7.17 (d, J=8.2 Hz, 2H), 7.32 (t, J=7.6 Hz, 1H).

$^{13}$C NMR (CDCl$_3$, 50 MHz): δ=54.6 (q), 103.8 (d), 112.4 (d), 113.8 (d), 123.7 (d), 131.1 (s), 139.1 (d), 148.5 (s), 155.9 (s), 156.4 (s).

HR-MS: Predicted [MH]$^+$=260.1394; Measured [MH]$^+$=260.1389.

EXAMPLE 43

3-(6-(4-Methoxyphenylamino)pyridin-2-ylamino)propan-1-ol

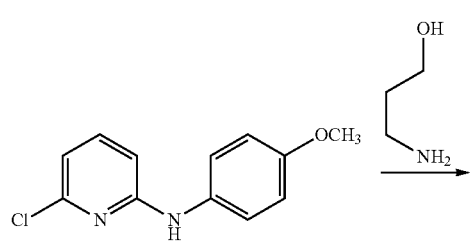

95 mg of 6-chloro-N-(4-methoxyphenyl)pyridin-2-amine were mixed with 244 mg of n-propanolamine and the mixture obtained was treated in a vial analogously to the method as set out in Example 16b. 3-(6-(4-Methoxyphenylamino)pyridin-2-ylamino)propan-1-ol was obtained in the form of a brown oil.

Yield: 64% of theory.

$^1$H NMR (CDCl$_3$, 200 MHz): δ=1.6-1.8 (m, 2H), 3.3 (t, J=6.3 Hz, 2H), 3.6 (t, J=5.8 Hz, 2H), 3.7 (s, 3H), 5.7 (d, J=8.0 Hz, 1H), 5.8 (d, J=8.4 Hz, 1H), 6.8 (d, J=9.2 Hz, 2H), 7.1 (d, J=8.8 Hz, 2H), 7.2 (t, J=8.2 Hz, 1H).

$^{13}$C NMR (CDCl$_3$, 50 MHz): δ=22.9 (t), 38.8 (t), 55.5 (q), 59.2 (t), 94.1 (d), 114.6 (d), 125.3 (d), 131.6 (s), 142.3 (d), 153.9 (s), 155.2 (d), 156.9 (s), 178.4 (s).

HR-MS: Predicted [MH]$^+$=274.1550; Measured [MH]$^+$=274.1555.

EXAMPLE 44

2-(6-(4-Phenoxyphenylamino)pyridin-2-ylamino)ethan-1-ol

44a. 6-Chloro-N-(4-phenoxyphenyl)pyridin-2-amine

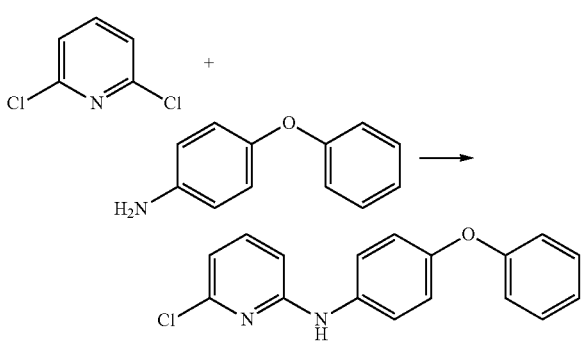

100 mg of 2,6-dichloropyridine, 150 mg of 4-phenoxyaniline, 329 mg of K$_2$CO$_3$, 3 mg of Pd(OAc)$_2$ and 9 mg of BINAP were charged into a microwave vial and 2.5 mL of dry toluene were added. The mixture obtained was treated in the vial analogously to the method as set out in Example 16a. For flash chromatography a solvent mixture of EtOAc:PE=1:10 was used. 6-Chloro-N-(4-phenoxyphenyl)pyridin-2-amine was obtained in the form of yellow crystals.

Yield: 77% of theory. M.p.: 69-73° C.

$^1$H NMR (CDCl$_3$, 200 MHz): δ=6.58-6.75 (q, J=7.2 Hz, 3H), 6.95-7.06 (m, 4H), 7.10 (d, J=7.4 Hz, 1H), 7.21-7.31 (m, 3H), 7.32-7.36 (m, 1H), 7.37-7.44 (m, 1H). $^{13}$C NMR (CDCl$_3$, 50 MHz): δ=105.3 (d), 113.9 (d), 118.5 (d), 120.0 (d), 123.2 (d), 123.6 (d), 129.8 (d), 134.8 (s), 140.0 (d), 149.7 (s), 153.5 (s), 156.7 (s), 157.5 (s).

Combustion Analysis: Calcd. C, 68.81%; H, 4.42%; N, 11.95%. Found: C, 68.60%; H, 4.225%; N, 8.92%.

44b. 2-(6-(4-Phenoxyphenylamino)pyridin-2-ylamino)ethan-1-ol

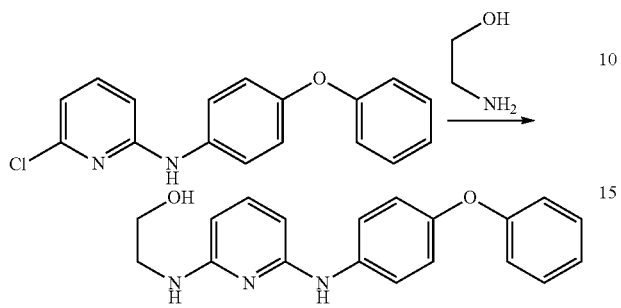

A mixture of 130 mg of 6-chloro-N-(4-phenoxyphenyl)pyridin-2-amine in 214 mg of ethanolamine was filled in a screw cap vial and was treated analogously to the method as set out in Example 16b, but using for flash column chromatography a solvent mixture of EtOAc:PE=1:1 instead of EtOAc:PE=3:1). 2-(6-(4-Phenoxyphenylamino)pyridin-2-ylamino)ethan-1-ol was obtained in the form of a brown oil.

Yield: 73% of theory.

$^1$H NMR (CDCl$_3$, 200 MHz): δ=3.30 (t, J=4.9 Hz, 2H), 3.8 (t, J=5.3 Hz, 2H), 5.8 (d, J=8.4 Hz, 1H), 5.9 (d, J=8.2 Hz, 1H), 6.8-7.4 (m, 11H).

$^{13}$C NMR (CDCl$_3$, 50 MHz): δ=45.2, 53.4, 60.4, 94.5, 118.7, 119.8, 123.4, 125.3, 129.8, 133.2, 143.8, 152.2, 153.7, 154.6, 157.2, 177.5.

EXAMPLE 45

3-(6-(4-Phenoxyphenylamino)pyridin-2-ylamino)propan-1-ol

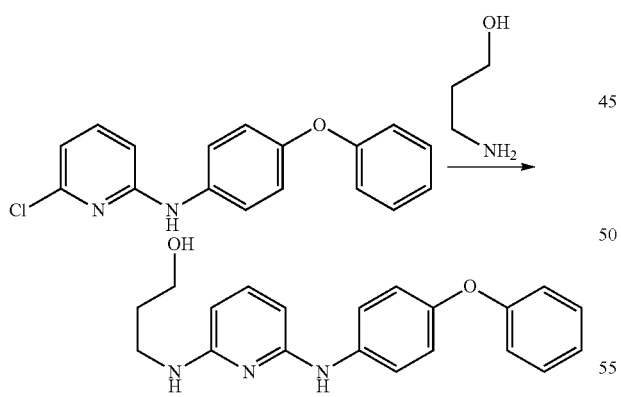

A mixture of 150 mg of 6-chloro-N-(4-phenoxyphenyl)pyridin-2-amine in 304 mg of n-propanolamine in a screw cap vial under argon was treated analogously to the method as set out in Example 16b. 3-(6-(4-Phenoxyphenylamino)pyridin-2-ylamino)propan-1-ol was obtained in the form of a brown oil.

Yield: 73% of theory.

$^1$H NMR (CDCl$_3$, 200 MHz): δ=1.8-1.9 (m, 2H), 3.4 (t, J=5.9 Hz, 2H), 3.7 (t, J=5.3 Hz, 2H), 5.9 (d, J=8.4 Hz, 1H), 6.0 (d, J=8.1 Hz, 1H), 6.9-7.4 (m, 11H).

The invention claimed is:

1. A process for producing a cardiomocyte-like cell, the process comprising:
   culturing a cell in the presence of a pyridine or pyrimidine compound of formula (I)

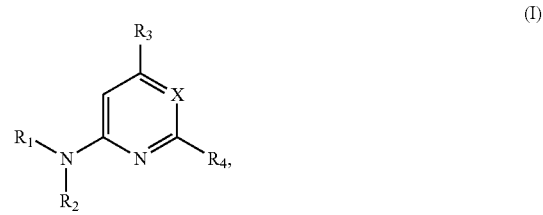

wherein
X is CH or N,
R$_1$ and R$_2$, independently of each other, are H, alkyl, aryl, or cycloalkyl,
R$_3$ and R$_4$, independently of each other, are H or NR$_5$R$_6$, and
R$_5$ and R$_6$, independently of each other, are H, alkyl, aryl, or cycloalkyl, or R$_1$ and R$_2$, together with the nitrogen atom to which they are attached, form an aromatic or aliphatic heterocyclic ring, wherein the aliphatic heterocyclic ring optionally comprises 1 to 4 heteroatoms selected from N, O, and S,
or R$_5$ and R$_6$, together with the nitrogen atom to which they are attached, form an aromatic or aliphatic heterocyclic ring, wherein the aliphatic heterocyclic ring optionally comprises 1 to 4 heteroatoms selected from N, O, and S,
wherein the alkyl, aryl, or cycloalkyl groups of R$_1$, R$_2$, R$_5$, and R$_6$ are substituted by 0 to 2 groups R$_{1a}$,
wherein the groups R$_{1a}$ are independently halogen, alkyl, alkoxy, —OH, —COOR$_{1b}$, —N(R$_{1b}$R$_{2b}$), heterocyclyl, —O-aryl, —N-aryl, or —NO$_2$,
wherein R$_{1b}$ and R$_{2b}$ are independently hydrogen or alkyl,
wherein cells to be cultured in the presence of the compound of formula (I) comprise omnipotent, pluripotent, skeletal muscle-committed cells, or a mixture thereof,
with the proviso that if X is N, R$_3$ is NR$_5$R$_6$ and R$_4$ is H, and if X is CH, one of R$_3$ and R$_4$ is NR$_5$R$_6$ and the other is H.

2. The process of claim 1, wherein the compound of formula (I) is present in the form of a salt.

3. The process of claim 1, wherein the compound of formula (I) is selected from the group consisting of
   (a) 2-(6-(4-Methoxyphenylamino)pyrimidine-4-ylamino)ethan-1-ol,
   (b) 3-(6-(4-Methoxyphenylamino)pyrimidine-4-ylamino)propan-1-ol,
   (c) N$^4$-Cyclohexyl-N$^6$-(4-methoxyphenyl)pyrimidine-4,6-diamine,
   (d) 2-(6-(4-Morpholinophenylamino)pyrimidin-4-ylamino)ethan-1-ol,
   (e) N$^4$-Cyclohexyl-N$^6$-(4-morpholinophenyl)pyrimidine-4,6-diamine,
   (f) 3-(6-(4-Morpholinophenylamino)pyrimidin-4-ylamino)propan-1-ol,
   (g) 2-(6-(4-(Phenylamino)phenylamino)pyrimidin-4-ylamino)ethan-1-ol,
   (h) 2-(6-(4-Phenoxyphenylamino)pyrimidin-4-ylamino)ethan-1-ol,
   (i) N$^4$-(4-Methoxyphenyl)-N$^6$-propylpyrimidine-4,6-diamine, (j) $N^4$-Ethyl-$N^6$-(4-methoxyphenyl)pyrimidine-4,6-diamine,
(k) $N^4$-(4-Methoxyphenyl)-$N^6$-methylpyrimidine-4,6-diamine,
(l) $N^4$-(2-Propyl)-$N^6$-(4-methoxyphenyl)pyrimidine-4,6-diamine,
(m) $N^4$-(2-Methoxyethyl)-$N^6$-(4-methoxyphenyl)pyrimidine-4,6-diamine,
(n) 2-(6-(4-Methoxyphenylamino)pyrimidin-4-ylamino)acetic acid,
(o) N-(4-Methoxyphenyl)-6-morpholinopyrimidin-4-amine,
(p) 2-((6-(4-Methoxyphenylamino)pyrimidin-4-yl)(methyl)amino)ethan-1-ol,
(q) $N^1$-Butyl-$N^6$-(4-methoxyphenyl)pyrimidine-4,6-diamine,
(r) $N^4$-Cyclopentyl-$N^6$-(4-methoxyphenyl)pyrimidine-4,6-diamine,
(s) $N^4$-sec-Butyl-$N^6$-(4-methoxyphenyl)pyrimidine-4,6-diamine,
(t) $N^4$-tert-Butyl-$N^6$-(4-methoxyphenyl)pyrimidine-4,6-diamine,
(u) $N^4$-Adamant-1-yl-$N^6$-(4-methoxyphenyl)pyrimidine-4,6-diamine,
(v) 2-(6-(3-Methoxyphenylamino)pyrimidin-4-ylamino)ethan-1-ol,
(w) 2-(6-(Phenylamino)pyrimidin-4-ylamino)ethan-1-ol,
(x) 2-(6-(4-Chlorophenylamino)pyrimidin-4-ylamino)ethan-1-ol,
(y) 2-(6-(3-Chlorophenylamino)pyrimidin-4-ylamino)ethan-1-ol,
(z) $N^4$-(3-Chlorophenyl)-$N^6$-cyclohexylpyrimidine-4,6-diamine,
(aa) $N^4$-(3-Chlorophenyl)-$N^6$-(2-methoxyethyl)pyrimidine-4,6-diamine,
(ab) 2-(6-(3-Nitrophenylamino)pyrimidin-4-ylamino)ethanol,
(ac) $N^4$-Cyclohexyl-$N^6$-(3-nitrophenyl)pyrimidine-4,6-diamine,
(ad) 2-(6-(4-Nitrophenylamino)pyrimidin-4-ylamino)ethan-1-ol,
(ae) 3-(6-(3-Chlorophenylamino)pyrimidin-4-ylamino)propan-1-ol,
(af) 2-(6-(3-Fluorophenylamino)pyrimidin-4-ylamino)ethan-1-ol,
(ag) 2-(6-(3-Bromophenylamino)pyrimidin-4-ylamino)ethan-1-ol,
(ah) Ethyl 4-(6-(2-hydroxyethylamino)pyrimidin-4-ylamino)benzoate,
(ai) 2-(6-(3-Chloro-4-methoxyphenylamino)pyrimidin-4-ylamino)ethanol,
(aj) $N^4$-(3-Chloro-4-methoxyphenyl)-$N^6$-cyclohexylpyrimidine-4,6-diamine,
(ak) $N^4$-Cyclohexyl-$N^6$-(3-methoxyphenyl)pyrimidine-4,6-diamine,
(al) 2-(6-((4-Methoxyphenyl)(methyl)amino)pyrimidin-4-ylamino)ethan-1-ol,
(am) 2-(6-(Cyclohexylamino)pyrimidin-4-ylamino)ethan-1-ol,
(an) 2-(4-(4-Methoxyphenylamino)pyridin-2-ylamino)ethan-1-ol,
(ao) 2-(4-(4-Phenoxyphenylamino)pyridin-2-ylamino)ethan-1-ol,
(ap) 2-(6-(4-Methoxyphenylamino)pyridin-2-ylamino)ethan-1-ol,
(aq) 3-(6-(4-Methoxyphenylamino)pyridin-2-ylamino)propan-1-ol,
(ar) 2-(6-(4-Phenoxyphenylamino)pyridin-2-ylamino)ethan-1-ol, and
(as) 3-(6-(4-Phenoxyphenylamino)pyridin-2-ylamino)propan-1-ol.

4. The process of claim 1, wherein the cardiomocyte-like cell comprises a cardiomocyte cell, a mammalian cell which expresses atrial natriuretic factor (ANF) characteristic of a cardiomocyte cell, or a mixture thereof.

5. The process of claim 1, wherein, in the compound of formula (I), at least one of $R_1$, $R_2$, $R_5$, and $R_6$ is
(i) $(C_{1-8})$alkyl,
(ii) $(C_{1-4}$ hydroxyalkyl,
(iii) $(C_{1-4})$alkoxy-$(C_{1-4})$alkyl,
(iv) carboxy$(C_{1-6})$alkyl, $(C_{3-12})$cycloalkyl,
(v) unsubstituted $(C_{6-12})$aryl, or
(vi) $(C_{6-12})$aryl substituted by one or more of $(C_{1-4})$alkoxy, nitro, halogen, $(C_{1-4})$alkoxycarbonyl, amino substituted by $(C_{6-12})$aryl, $(C_{6-12})$aryloxy, and heterocyclyl comprising 3 to 8 ring members and 1 to 4 heteroatoms independently selected from N, O, and S.

6. The process of claim 1, wherein the compound of formula (I) is selected from the group consisting of
(a) 2-(6-(4-Methoxyphenylamino)pyrimidine-4-ylamino)ethan-1-ol,
(b) 3-(6-(4-Methoxyphenylamino)pyrimidine-4-ylamino)propan-1-ol,
(c) $N^4$-Cyclohexyl-$N^6$-(4-methoxyphenyl)pyrimidine-4,6-diamine,
(d) 2-(6-(4-Morpholinophenylamino)pyrimidin-4-ylamino)ethan-1-ol,
(e) $N^4$-Cyclohexyl-$N^6$-(4-morpholinophenyl)pyrimidine-4,6-diamine, and
(f) 3-(6-(4-Morpholinophenylamino)pyrimidin-4-ylamino)propan-1-ol.

7. The process of claim 1, wherein the compound of formula (I) is selected from the group consisting of
(g) 2-(6-(4-(Phenylamino)phenylamino)pyrimidin-4-ylamino)ethan-1-ol,
(h) 2-(6-(4-Phenoxyphenylamino)pyrimidin-4-ylamino)ethan-1-ol,
(i) $N^4$-(4-Methoxyphenyl)-$N^6$-propylpyrimidine-4,6-diamine,
(j) $N^4$-Ethyl-$N^6$-(4-methoxyphenyl)pyrimidine-4,6-diamine,
(k) $N^4$-(4-Methoxyphenyl)-$N^6$-methylpyrimidine-4,6-diamine, and
(l) $N^4$-(2-Propyl)-$N^6$-(4-methoxyphenyl)pyrimidine-4,6-diamine.

8. The process of claim 1, wherein the compound of formula (I) is selected from the group consisting of
(m) $N^4$-(2-Methoxyethyl)-$N^6$-(4-methoxyphenyl)pyrimidine-4,6-diamine,
(n) 2-(6-(4-Methoxyphenylamino)pyrimidin-4-ylamino)acetic acid,
(o) N-(4-Methoxyphenyl)-6-morpholinopyrimidin-4-amine,
(p) 2-((6-(4-Methoxyphenylamino)pyrimidin-4-yl)(methyl)amino)ethan-1-ol,
(q) $N^4$-Butyl-$N^6$-(4-methoxyphenyl)pyrimidine-4,6-diamine, and
(r) $N^4$-Cyclopentyl-$N^6$-(4-methoxyphenyl)pyrimidine-4,6-diamine.

9. The process of claim 1, wherein the compound of formula (I) is selected from the group consisting of
(s) $N^4$-sec-Butyl-$N^6$-(4-methoxyphenyl)pyrimidine-4,6-diamine, (t) $N^4$-tert-Butyl-$N^6$-(4-methoxyphenyl)pyrimidine-4,6-diamine,
(u) $N^4$-Adamant-1-yl-$N^6$-(4-methoxyphenyl)pyrimidine-4,6-diamine,
(v) 2-(6-(3-Methoxyphenylamino)pyrimidin-4-ylamino)ethan-1-ol,
(w) 2-(6-(Phenylamino)pyrimidin-4-ylamino)ethan-1-ol, and
(x) 2-(6-(4-Chlorophenylamino)pyrimidin-4-ylamino)ethan-1-ol.

10. The process of claim 1, wherein the compound of formula (I) is selected from the group consisting of
(y) 2-(6-(3-Chlorophenylamino)pyrimidin-4-ylamino)ethan-1-ol,
(z) $N^4$-(3-Chlorophenyl)-$N^6$-cyclohexylpyrimidine-4,6-diamine, and
(aa) $N^4$-(3-Chlorophenyl)-$N^6$-(2-methoxyethyl)pyrimidine-4,6-diamine.

11. The process of claim 1, wherein the compound of formula (I) is selected from the group consisting of
(ab) 2-(6-(3-Nitrophenylamino)pyrimidin-4-ylamino)ethanol,
(ac) $N^4$-Cyclohexyl-$N^6$-(3-nitrophenyl)pyrimidine-4,6-diamine,
(ad) 2-(6-(4-Nitrophenylamino)pyrimidin-4-ylamino)ethan-1-ol,
(ae) 3-(6-(3-Chlorophenylamino)pyrimidin-4-ylamino)propan-1-ol,
(af) 2-(6-(3-Fluorophenylamino)pyrimidin-4-ylamino)ethan-1-ol, and
(ag) 2-(6-(3-Bromophenylamino)pyrimidin-4-ylamino)ethan-1-ol.

12. The process of claim 1, wherein the compound of formula (I) is selected from the group consisting of
(ah) Ethyl 4-(6-(2-hydroxyethylamino)pyrimidin-4-ylamino)benzoate,
(ai) 2-(6-(3-Chloro-4-methoxyphenylamino)pyrimidin-4-ylamino)ethanol,
(aj) $N^4$-(3-Chloro-4-methoxyphenyl)-$N^6$-cyclohexylpyrimidine-4,6-diamine,
(ak) $N^4$-Cyclohexyl-$N^6$-(3-methoxyphenyl)pyrimidine-4,6-diamine,
(al) 2-(6-((4-Methoxyphenyl)(methyl)amino)pyrimidin-4-ylamino)ethan-1-ol, and
(am) 2-(6-(Cyclohexylamino)pyrimidin-4-ylamino)ethan-1-ol.

13. The process of claim 1, wherein the compound of formula (I) is selected from the group consisting of
(an) 2-(4-(4-Methoxyphenylamino)pyridin-2-ylamino)ethan-1-ol,
(ao) 2-(4-(4-Phenoxyphenylamino)pyridin-2-ylamino)ethan-1-ol,
(ap) 2-(6-(4-Methoxyphenylamino)pyridin-2-ylamino)ethan-1-ol,
(aq) 3-(6-(4-Methoxyphenylamino)pyridin-2-ylamino)propan-1-ol,
(ar) 2-(6-(4-Phenoxyphenylamino)pyridin-2-ylamino)ethan-1-ol, and
(as) 3-(6-(4-Phenoxyphenylamino)pyridin-2-ylamino)propan-1-ol.

14. The process of claim 1, wherein the cardiomyocyte-like cell obtained has an altered expression of atrial natriuretic factor relative to an untreated omnipotent, pluripotent, or skeletal muscle-committed cell.

15. The process of claim 14, wherein the cardiomyocyte-like cell obtained has an altered expression of Nkx2.5 relative to an untreated omnipotent, pluripotent, or skeletal muscle-committed cell.

16. The process of claim 1, wherein the cardiomyocyte-like cell obtained has an up-regulated expression of atrial natriuretic factor relative to an untreated omnipotent, pluripotent, or skeletal muscle-committed cell.

17. The process of claim 1, wherein the cardiomyocyte-like cell obtained has an altered expression of Nkx2.5 relative to an untreated omnipotent, pluripotent, or skeletal muscle-committed cell.

18. The process of claim 1, wherein the cardiomyocyte-like cell obtained has an up-regulated expression of Nkx2.5 relative to an untreated omnipotent, pluripotent, or skeletal muscle-committed cell.

19. The process of claim 1, wherein the cardiomyocyte-like cell obtained has an altered expression of transcription control factor activity as indicated by a TOPflash luciferase reporter plasmid.

\* \* \* \* \*